US012679808B2

(12) United States Patent
Schotes et al.

(10) Patent No.: US 12,679,808 B2
(45) **Date of Patent: *Jul. 14, 2026**

(54) ENANTIOSELECTIVE HYDROGENATION OF 4-SUBSTITUTED 1,2-DIHYDROQUINOLINES IN PRESENCE OF A CHIRAL IRIDIUM CATALYST AND AN ADDITIVE

(71) Applicant: Bayer Aktiengesellschaft, Leverkusen (DE)

(72) Inventors: Christoph Schotes, Duesseldorf (DE); Matthias Beller, Nienhagen (DE); Kathrin Junge, Rostock (DE); Weiping Liu, Shanghai (CN); Jacob Schneekoenig, Leipzig (DE); Thomas Leischner, Rostock (DE)

(73) Assignee: Bayer Aktiengesellschaft, Leverkusen (DE)

( * ) Notice: Subject to any disclaimer, the term of this patent is extended or adjusted under 35 U.S.C. 154(b) by 1147 days.

This patent is subject to a terminal disclaimer.

(21) Appl. No.: 17/639,266

(22) PCT Filed: Sep. 22, 2020

(86) PCT No.: PCT/EP2020/076373

§ 371 (c)(1),
(2) Date: Feb. 28, 2022

(87) PCT Pub. No.: WO2021/058457

PCT Pub. Date: Apr. 1, 2021

(65) Prior Publication Data

US 2022/0306583 A1 Sep. 29, 2022

(30) Foreign Application Priority Data

Sep. 25, 2019 (EP) .................................... 19199632

(51) Int. Cl.
*C07D 215/12* (2006.01)
*B01J 31/22* (2006.01)
*C07D 215/08* (2006.01)

(52) U.S. Cl.
CPC ............ *C07D 215/12* (2013.01); *B01J 31/22* (2013.01); *C07D 215/08* (2013.01); *C07B 2200/07* (2013.01)

(58) Field of Classification Search
CPC ............................ C07D 215/12; C07D 215/08
See application file for complete search history.

(56) References Cited

U.S. PATENT DOCUMENTS

2017/0022162 A1 1/2017 Takahashi et al.
2017/0150717 A1 6/2017 Dubost et al.
2021/0009521 A1 1/2021 Schotes et al.
2022/0324810 A1* 10/2022 Schotes ................ C07D 215/08

FOREIGN PATENT DOCUMENTS

EP 0654464 A1 5/1995
EP 3103789 A1 12/2016
WO 2011162397 A1 12/2011
WO 2012084812 A1 6/2012
WO 2014096065 A1 6/2014
WO 2015141564 A1 9/2015
WO 2015197530 A1 12/2015
WO 2019185541 A1 10/2019

OTHER PUBLICATIONS

Schneekönig et al., Organic Process Research & Development (Feb. 20, 2020), 24(3), 443-447 and Supporting Information on pp. 1-33. (Year: 2020).*
PCT International Search Report for PCT/EP2020/076373, mailed Nov. 30, 2020.
Liu et al: "Synthesis of tunable phosphinite-pyridine ligands and their applications in asymmetric hydrogenation", Tetrahedron Letters, Elsevier Ltd, Amsterdan, NL, vol. 47, No. 27, Apr. 3, 2006, pp. 4733-4736, XP025004390.
David H Woodmansee et al: "Chiral pyridyl phosphinites with large aryl substituents as efficient ligands for the asymmetric iridium-catalyzed hydrogenation of difficult substrates", Chemical Science, Royal Society of Chemistry, United Kingdom, vol. 1, May 1, 2010, pp. 72-78, XP002662994.
Wiliam J. Drury et al.: "Synthesis of Versatile Chiral N, P Ligands Derived from Pyridine and Quinoline", Angewandte Chemie, International Edition, vol. 43, No. 1, Jan. 1, 2004, pp. 70-74, XP055485442.
Alejandro Baeza et al: "Iridum-Catalyzed Asymmetric Hydrogenation of N-Protected Indoles", Chemistry—A European Journal, vol. 16, No. 7, Feb. 15, 2010, pp. 2036-2039, XP055225292.
Pauli, Larissa, et al. "Asymmetric hydrogenation of furans and benzofurans with Iridium-Pyridine-Phosphinite catalysts." Chemistry—A European Journal, (2015), vol. 21, No. 4: 1482-1487.
Kaiser et al., "Iridium Catalysts with Bicyclic Pyridine-Phosphinite Ligands: Asymmetric Hydrogenation of Olefins and Furan Derivatives", Angew. Chem. Int. Ed., 2006, vol. 45, pp. 5194-5197.
Pauli,et al., "Asymmetric Hydrogenation of Furans and Benzofurans with Iridium Pyridine Phosphinite Catalysts," Chemistry: A European Journal vol. 21, pp. 1482-1487 (2015).

* cited by examiner

*Primary Examiner* — Laura L Stockton

(57) ABSTRACT

The invention relates to a process for preparing optically active 4-substituted 1,2,3,4-tetrahydroquinolines comprising enantioselective hydrogenation of the corresponding 4-substituted 1,2-dihydroquinolines in presence of a chiral iridium (P,N)-ligand catalyst and an additive.

12 Claims, No Drawings

ENANTIOSELECTIVE HYDROGENATION OF 4-SUBSTITUTED 1,2-DIHYDROQUINOLINES IN PRESENCE OF A CHIRAL IRIDIUM CATALYST AND AN ADDITIVE

CROSS-REFERENCE TO RELATED APPLICATIONS

This application is the National Stage entry of International Application No. PCT/EP2020/076373, filed 22 Sep. 2020, which claims priority to European Patent Application No. 19199632.1, filed 25 Sep. 2019.

BACKGROUND

Field

The invention relates to a process for preparing optically active 4-substituted 1,2,3,4-tetrahydroquinolines comprising enantioselective hydrogenation of the corresponding 4-substituted 1,2-dihydroquinolines in presence of a chiral iridium (P,N)-ligand catalyst and an additive.

Description of Related Art

It is known from EP 0 654 464 that N-acetyl-tetrahydroquinolines can be converted to the corresponding 4-aminoindane derivatives via a rearrangement reaction.

4-aminoindane derivatives are important intermediates for preparing various N-indanyl heteroaryl carboxamides having fungicidal activity (EP 0 654 464, WO 2011/162397, WO 2012/084812, WO 2015/197530).

EP 3 103 789 discloses a method for optically resolving 1,1,3-trimethyl-4-aminoindane by converting the enantiomeric mixture into the diastereomeric salts of D-tartaric acid. (R)- and (S)-1,1,3-trimethyl-4-aminoindane are obtained after separation and basification of the diastereomeric salts. This reference also discloses a method for racemizing the undesired enantiomer, so that the whole method allows for converting the undesired enantiomer into the desired enantiomer via several process steps. (R)-1,1,3-trimethyl-4-aminoindane is an important intermediate for preparing the pyrazole carboxamide fungicide inpyrfluxam.

A method for preparing chiral intermediates of N-indanyl heteroaryl carboxamides via asymmetric synthesis is also known. WO 2015/141564 describes a process for preparing optically active 4-substituted 1,2,3,4-tetrahydroquinolines, which process comprises the hydrogenation of the corresponding 4-substituted 1,2-dihydroquinolines in presence of a transition metal catalyst having an optically active ligand. The asymmetric hydrogenation of the 4-substituted NH-dihydroquinolines proceeded with moderate conversion rates (up to 62.6%) and enantioselectivity (up to 71.3% ee), whereas N-acetyl-dihydroquinolines gave even poorer conversion (up to 14%) and enantioselectivity (up to 31% ee).

SUMMARY

In the light of the prior art described above, it is an object of the present invention to provide a process for preparing optically active 4-substituted 1,2,3,4-tetrahydroquinolines which process has advantages over the processes of the prior art. The process should allow the desired enantiomer to be prepared in high yield and high enantiomeric purity, with few process steps and few purification steps.

The object described above was achieved by a process for preparing a compound of the formula (Ta) or (Ib),

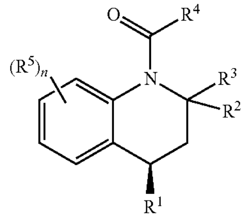

(Ia)

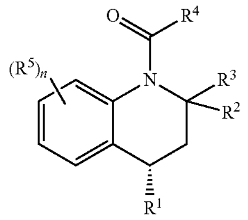

(Ib)

wherein $R^1$ is selected from the group consisting of $C_1$-$C_6$-alkyl, $C_1$-$C_6$-haloalkyl, $C_1$-$C_6$-alkoxy-$C_1$-$C_6$-alkyl, $C_3$-$C_6$-cycloalkyl, $C_6$-$C_{14}$-aryl, or $C_6$-$C_{14}$-aryl-$C_1$-$C_4$-alkyl,
- wherein the $C_1$-$C_6$-alkyl, $C_3$-$C_6$-cycloalkyl and the $C_1$-$C_6$-alkoxy in the $C_1$-$C_6$-alkoxy-$C_1$-$C_6$-alkyl moiety, are optionally substituted by 1 to 3 substituents independently selected from the group consisting of halogen, $C_1$-$C_4$-alkoxy, $C_1$-$C_4$-haloalkyl, $C_1$-$C_4$-haloalkoxy and phenyl, wherein the phenyl may be substituted by one to five substituents selected independently from each other from halogen, $C_1$-$C_4$-alkyl, $C_1$-$C_4$-alkoxy, $C_1$-$C_4$-haloalkyl, and $C_1$-$C_4$-haloalkoxy, and
- wherein the $C_6$-$C_{14}$-aryl and the $C_6$-$C_{14}$-aryl in the $C_6$-$C_{14}$-aryl-$C_1$-$C_4$-alkyl moiety in each case is unsubstituted or substituted by one to five substituents selected from the group consisting of halogen, $C_1$-$C_4$-alkyl, $C_1$-$C_4$-haloalkyl, $C_1$-$C_4$-alkoxy and $C_1$-$C_4$-haloalkoxy, $R^2$ and $R^3$ are the same and are selected from the group consisting of hydrogen, $C_1$-$C_6$-alkyl, $C_1$-$C_6$-haloalkyl and $C_1$-$C_6$-alkoxy-$C_1$-$C_6$-alkyl, or $R^2$ and $R^3$ together with the carbon which they are bound to, form a $C_3$-$C_6$-cycloalkyl ring, $R^4$ is hydrogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylamino, $C_2$-$C_6$-alkenyl, $C_2$-$C_6$-alkynyl, $C_3$-$C_6$-cycloalkyl, $C_3$-$C_6$-cycloalkyl-$C_1$-$C_4$-alkyl, $C_2$-$C_6$-alkenyloxy, 9-flurorenylmethyleneoxy, $C_6$-$C_{14}$-aryl, $C_6$-$C_{14}$-aryloxy, $C_6$-$C_{14}$-aryl-$C_1$-$C_4$-alkyloxy or $C_6$-$C_{14}$-aryl-$C_1$-$C_4$-alkyl,
- wherein the $C_6$-$C_{14}$-aryl as such or as part of a composite substituent is unsubstituted or substituted by one to five substituents selected from the group consisting of halogen, $C_1$-$C_4$-alkyl, $C_1$-$C_4$-haloalkyl, $C_1$-$C_4$-alkoxy and $C_1$-$C_4$-haloalkoxy, n is 0, 1, 2, 3 or 4, each substituent $R^5$, if present, is independently selected from the group consisting of halogen, $C_1$-$C_6$-alkyl, $C_1$-$C_6$-haloalkyl, $C_1$-$C_6$-alkoxy, hydroxyl, amino and —C(═O)—$C_1$-$C_6$-alkyl, comprising enantioselective hydrogenation of a compound of the formula (II)

(II)

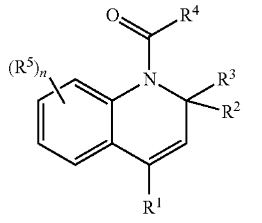

wherein the substituents $R^1$, $R^2$, $R^3$, $R^4$, $R^5$ and the integer n are each as defined for the compound of the formula (Ia) or (Ib), in presence of a chiral iridium catalyst, characterized in that the chiral iridium catalyst comprises a chiral ligand of the formula (IIIa), (IIIb), (IVa) (IVb), (IXa), or (IXb)

(IIIa)

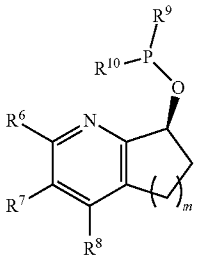

(IIIb)

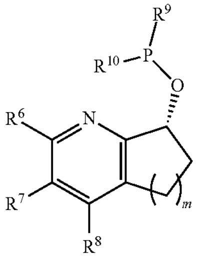

(IVa)

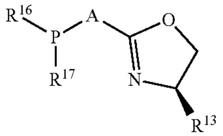

(IVb)

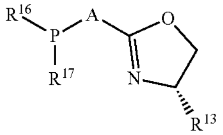

(IXa)

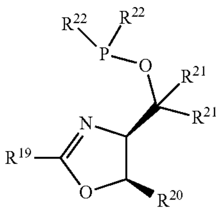

-continued (IXb)

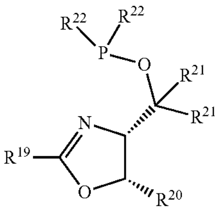

wherein $R^6$, $R^7$ and $R^8$ are independently from one another selected from the group consisting of hydrogen, halogen, $C_1$-$C_6$-alkyl, $C_1$-$C_6$-haloalkyl, $C_1$-$C_6$-alkoxy, $C_2$-$C_6$-alkenyl, $C_2$-$C_6$-alkynyl, $C_3$-$C_7$-cycloalkyl, $C_3$-$C_7$-cycloalkyl-$C_1$-$C_4$-alkyl, $C_6$-$C_{14}$-aryl and $C_6$-$C_{14}$-aryl-$C_1$-$C_4$-alkyl, wherein the $C_1$-$C_6$-alkyl, $C_2$-$C_6$-alkenyl, $C_2$-$C_6$-alkynyl, $C_3$-$C_7$-cycloalkyl and the $C_3$-$C_7$-cycloalkyl in the $C_3$-$C_7$-cycloalkyl-$C_1$-$C_4$-alkyl moiety are optionally substituted by 1 to 3 substituents independently selected from the group consisting of halogen, $C_1$-$C_4$-alkyl, $C_1$-$C_4$-alkoxy and $C_1$-$C_4$-haloalkyl and $C_1$-$C_4$-haloalkoxy, and wherein the $C_6$-$C_{14}$-aryl and the $C_6$-$C_{14}$-aryl in the $C_6$-$C_{14}$-aryl-$C_1$-$C_4$-alkyl moiety are optionally substituted by one to five substituents selected from the group consisting of halogen, $C_1$-$C_4$-alkyl, $C_1$-$C_4$-haloalkyl, $C_1$-$C_4$-alkoxy, $C_1$-$C_4$-haloalkoxy and phenyl, wherein the phenyl again is unsubstituted or substituted by one to five $C_1$-$C_6$-alkyl substituents, $R^9$ and $R^{10}$ are independently from one another selected from the group consisting of $C_1$-$C_6$-alkyl, $C_2$-$C_6$-alkenyl, $C_2$-$C_6$-alkynyl, $C_1$-$C_6$-alkoxy, di($C_1$-$C_6$-alkyl)amino, $C_3$-$C_{12}$-cycloalkyl, $C_3$-$C_{12}$-cycloalkyl-$C_1$-$C_4$-alkyl, $C_6$-$C_{14}$-aryl, $C_6$-$C_{14}$-aryloxy and $C_6$-$C_{14}$-aryl-$C_1$-$C_4$-alkyl, wherein the $C_1$-$C_6$-alkyl, $C_2$-$C_6$-alkenyl, $C_2$-$C_6$-alkynyl, $C_1$-$C_6$-alkoxy and di($C_1$-$C_6$-alkyl)amino, are optionally substituted by 1 to 3 substituents independently selected from the group consisting of halogen, $C_1$-$C_4$-alkoxy, $C_1$-$C_4$-haloalkyl, $C_1$-$C_4$-haloalkoxy and phenyl, wherein the phenyl may be substituted by one to five substituents selected independently from each other from halogen, $C_1$-$C_4$-alkyl, $C_1$-$C_4$-alkoxy, $C_1$-$C_4$-haloalkyl, and $C_1$-$C_4$-haloalkoxy, and wherein the $C_6$-$C_{14}$-aryl, $C_6$-$C_{14}$-aryloxy and $C_3$-$C_{12}$-cycloalkyl, in each case as such or as part of a composite substituent, are optionally substituted by one to five substituents selected from the group consisting of halogen, $C_1$-$C_4$-alkyl, $C_1$-$C_4$-haloalkyl, $C_1$-$C_4$-alkoxy, $C_1$-$C_4$-haloalkoxy and phenyl, wherein the phenyl is unsubstituted or substituted by one to five $C_1$-$C_6$-alkyl substituents or $R^9$ and $R^{10}$ together with the phosphorus atom which they are bound to, form a phospholane ring, which may be substituted with one or two $C_1$-$C_6$-alkyl groups, or $R^9$ and $R^{10}$ together form $G^1$ = 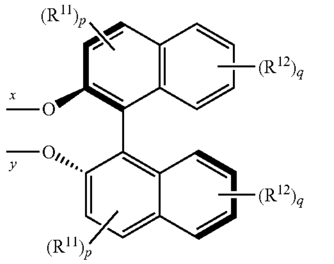 or $G^2$ = 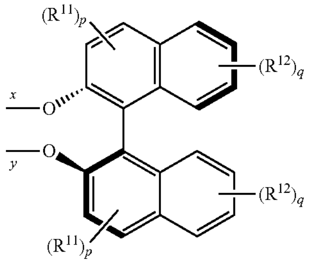

in which the bonds identified by "x" and "y" are both bound directly to the phosphorus atom, p and q are independently from one another selected from 0, 1 and 2, $R^{11}$ and $R^{12}$ are independently selected from $C_1$-$C_6$-alkyl and phenyl, which may be substituted by one to five substituents selected from the group consisting of halogen, $C_1$-$C_4$-alkyl, $C_1$-$C_4$-alkoxy and phenyl, which may be substituted by one or two $C_1$-$C_4$-alkyl substituents, m is 1 or 2, A is $A^1$ = 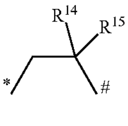 or $A^2$ = 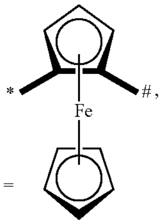

in which the bond identified by * is bound directly to the phosphorus atom and in which the bond identified by "#" is bound directly to the oxazoline moiety, $R^{13}$ is $C_1$-$C_6$-alkyl, $C_1$-$C_6$-haloalkyl, $C_3$-$C_{12}$-cycloalkyl, $C_3$-$C_{12}$-cycloalkyl-$C_1$-$C_4$-alkyl, $C_1$-$C_4$-alkyl-$C_3$-$C_7$-cycloalkyl, $C_6$-$C_{14}$-aryl or $C_6$-$C_{14}$-aryl-$C_1$-$C_4$-alkyl, wherein the $C_6$-$C_{14}$-aryl and the $C_6$-$C_{14}$-aryl in the $C_6$-$C_{14}$-aryl-$C_1$-$C_4$-alkyl moiety in each case is unsubstituted or substituted by one to five substituents selected from the group consisting of halogen, $C_1$-$C_4$-alkyl, $C_1$-$C_4$-haloalkyl, $C_1$-$C_4$-alkoxy and $C_1$-$C_4$-haloalkoxy, $R^{14}$ and $R^{15}$ are independently from one another selected from the group consisting of hydrogen, $C_1$-$C_6$-alkyl, $C_1$-$C_6$-haloalkyl, $C_3$-$C_{12}$-cycloalkyl, $C_3$-$C_7$-cycloalkyl-$C_1$-$C_4$-alkyl, $C_1$-$C_4$-alkyl-$C_3$-$C_7$-cycloalkyl, $C_6$-$C_{14}$-aryl and $C_6$-$C_{14}$-aryl-$C_1$-$C_4$-alkyl, wherein the $C_6$-$C_{14}$-aryl and the $C_6$-$C_{14}$-aryl in the $C_6$-$C_{14}$-aryl-$C_1$-$C_4$-alkyl moiety in each case is unsubstituted or substituted by one to five substituents selected from the group consisting of halogen, $C_1$-$C_4$-alkyl, $C_1$-$C_4$-haloalkyl, $C_1$-$C_4$-alkoxy and $C_1$-$C_4$-haloalkoxy, or $R^{14}$ and $R^{15}$ together with the carbon which they are bound to, form a $C_5$-$C_6$-cycloalkyl ring, $R^{16}$ and $R^{17}$ are independently from one another selected from the group consisting of $C_1$-$C_6$-alkyl, $C_2$-$C_6$-alkenyl, $C_2$-$C_6$-alkynyl, $C_1$-$C_6$-alkoxy, di($C_1$-$C_6$-alkyl)amino, $C_3$-$C_{12}$-cycloalkyl, $C_3$-$C_{12}$-cycloalkyl-$C_1$-$C_4$-alkyl, $C_6$-$C_{14}$-aryl, $C_6$-$C_{14}$-aryloxy and $C_6$-$C_{14}$-aryl-$C_1$-$C_4$-alkyl, wherein the $C_1$-$C_6$-alkyl, $C_2$-$C_6$-alkenyl, $C_2$-$C_6$-alkynyl, $C_1$-$C_6$-alkoxy, $C_1$-$C_6$-cycloalkyl and di($C_1$-$C_6$-alkyl)amino, are optionally substituted by 1 to 3 substituents independently selected from the group consisting of halogen, $C_1$-$C_4$-alkoxy, $C_1$-$C_4$-haloalkyl, $C_1$-$C_4$-haloalkoxy and phenyl, wherein the phenyl may be substituted by one to five substituents selected independently from each other from halogen, $C_1$-$C_4$-alkyl, phenyl, $C_1$-$C_4$-alkoxy, $C_1$-$C_4$-haloalkyl, and $C_1$-$C_4$-haloalkoxy, and wherein the $C_6$-$C_{14}$-aryl, the $C_6$-$C_{14}$-aryl in the $C_6$-$C_{14}$-aryl-$C_1$-$C_4$-alkyl, the $C_6$-$C_{14}$-aryloxy and $C_3$-$C_{12}$-cycloalkyl, in each case as such or as part of a composite substituent, are optionally substituted by one to five substituents selected from the group consisting of halogen, $C_1$-$C_4$-alkyl, phenyl, $C_1$-$C_4$-haloalkyl, $C_1$-$C_4$-alkoxy and $C_1$-$C_4$-haloalkoxy, or $R^{16}$ and $R^{17}$ together with the phosphorus atom which they are bound to, form a phospholane ring, which may be substituted with one or two $C_1$-$C_6$-alkyl groups, or $R^{16}$ and $R^{17}$ together form $G^1$ = 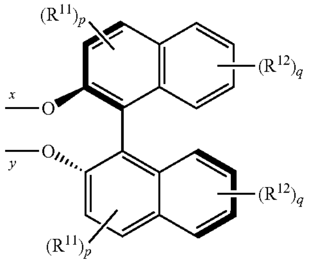 or $G^2$ = 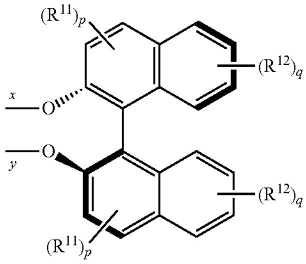

in which the bonds identified by "x" and "y" are both bound directly to the phosphorus atom, p and q are independently from one another selected from 0, 1 and 2, $R^{11}$ and $R^{12}$ are independently selected from $C_1$-$C_6$-alkyl and phenyl, which may be substituted by one to five substituents selected from the group consisting of halogen, $C_1$-$C_4$-alkyl, $C_1$-$C_4$-alkoxy and phenyl, which may be substituted by one or two $C_1$-$C_4$-alkyl substituents, $R_{19}$ are independently selected from phenyl, benzyl, t-butyl, isopropyl, cyclohexyl, $R^{20}$ are independently selected from hydrogen, methyl, ethyl, isopropyl, $R^{21}$ are independently selected from hydrogen, benzyl, methyl, ethyl $R^{22}$ are independently selected from cyclohexyl, phenyl, 2-methylphenyl, 4-methylphenyl, 2,6-dimethylphenyl, 3,5-dimethylphenyl, 2,4,6-trimethylphenyl, and in the presence of an additive, wherein the additive is selected from the group consisting of Brsnsted acids, Lewis acids, and mixtures thereof.

DETAILED DESCRIPTION OF A PREFERRED EMBODIMENT

It has been found, surprisingly, that optically active 4-substituted 1,2,3,4-tetrahydroquinolines (Ia and Ib) can be prepared in high yields and excellent enantioselectivity by enantioselective hydrogenation of the corresponding 4-substituted 1,2-dihydroquinolines (II) in presence of a chiral iridium (P,N)-ligand catalyst and an additive.

Definitions

In the definitions of the symbols given in the above formulae, collective terms were used, which are generally representative of the following substituents:

Halogen: fluorine, chlorine, bromine or iodine, preferably fluorine, chlorine or bromine, and more preferably fluorine or chlorine.

Alkyl: saturated, straight-chain or branched hydrocarbyl substituents having 1 to 6, preferably 1 to 4 carbon atoms, for example (but not limited to) $C_1$-$C_6$-alkyl such as methyl, ethyl, propyl (n-propyl), 1-methylethyl (iso-propyl), butyl (n-butyl), 1-methylpropyl (sec-butyl), 2-methylpropyl (iso-butyl), 1,1-dimethylethyl (tert-butyl), pentyl, 1-methylbutyl, 2-methylbutyl, 3-methylbutyl, 2,2-dimethylpropyl, 1-ethylpropyl, 1,1-dimethylpropyl, 1,2-dimethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2, 2-trimethylpropyl, 1-ethyl-1-methylpropyl and 1-ethyl-2-methylpropyl. Particularly, said group is a $C_1$-$C_4$-alkyl group, e.g. a methyl, ethyl, propyl, 1-methylethyl (isopropyl), butyl, 1-methylpropyl (sec-butyl), 2-methylpropyl (iso-butyl) or 1,1-dimethylethyl (tert-butyl) group. This definition also applies to alkyl as part of a composite substituent, for example $C_3$-$C_6$-cycloalkyl-$C_1$-$C_4$-alkyl, $C_6$-$C_{14}$-aryl-$C_1$-$C_4$-alkyl etc., unless defined elsewhere.

Alkenyl: unsaturated, straight-chain or branched hydrocarbyl substituents having 2 to 6, preferably 2 to 4 carbon atoms and one double bond in any position, for example (but not limited to) $C_2$-$C_6$-alkenyl such as vinyl, allyl, (E)-2-methylvinyl, (Z)-2-methylvinyl, isopropenyl, homoallyl, (E)-but-2-enyl, (Z)-but-2-enyl, (E)-but-1-enyl, (Z)-but-1-enyl, 2-methylprop-2-enyl, 1-methylprop-2-enyl, 2-methylprop-1-enyl, (E)-1-methylprop-1-enyl, (Z)-1-methylprop-1-enyl, pent-4-enyl, (E)-pent-3-enyl, (Z)-pent-3-enyl, (E)-pent-2-enyl, (Z)-pent-2-enyl, (E)-pent-1-enyl, (Z)-pent-1-enyl, 3-methylbut-3-enyl, 2-methylbut-3-enyl, 1-methylbut-3-enyl, 3-methylbut-2-enyl, (E)-2-methylbut-2-enyl, (Z)-2-methylbut-2-enyl, (E)-1-methylbut-2-enyl, (Z)-1-methylbut-2-enyl, (E)-3-methylbut-1-enyl, (Z)-3-methylbut-1-enyl, (E)-2-methylbut-1-enyl, (Z)-2-methylbut-1-enyl, (E)-1-methylbut-1-enyl, (Z)-1-methylbut-1-enyl, 1,1-dimethylprop-2-enyl, 1-ethylprop-1-enyl, 1-propylvinyl, 1-isopropylvinyl, (E)-3,3-dimethylprop-1-enyl, (Z)-3,3-dimethylprop-1-enyl, hex-5-enyl, (E)-hex-4-enyl, (Z)-hex-4-enyl, (E)-hex-3-enyl, (Z)-hex-3-enyl, (E)-hex-2-enyl, (Z)-hex-2-enyl, (E)-hex-1-enyl, (Z)-hex-1-enyl, 4-methylpent-4-enyl, 3-methylpent-4-enyl, 2-methylpent-4-enyl, 1-methylpent-4-enyl, 4-methylpent-3-enyl, (E)-3-methylpent-3-enyl, (Z)-3-methylpent-3-enyl, (E)-2-methylpent-3-enyl, (Z)-2-methylpent-3-enyl, (E)-1-methylpent-3-enyl, (Z)-1-methylpent-3-enyl, (E)-4-methylpent-2-enyl, (Z)-4-methylpent-2-enyl, (E)-3-methylpent-2-enyl, (Z)-3-methylpent-2-enyl, (E)-2-methylpent-2-enyl, (Z)-2-methylpent-2-enyl, (E)-1-methylpent-2-enyl, (Z)-1-methylpent-2-enyl, (E)-4-methylpent-1-enyl, (Z)-4-methylpent-1-enyl, (E)-3-methylpent-1-enyl, (Z)-3-methylpent-1-enyl, (E)-2-methylpent-1-enyl, (Z)-2-methylpent-1-enyl, (E)-1-methylpent-1-enyl, (Z)-1-methylpent-1-enyl, 3-ethylbut-3-enyl, 2-ethylbut-3-enyl, 1-ethylbut-3-enyl, (E)-3-ethylbut-2-enyl, (Z)-3-ethylbut-2-enyl, (E)-2-ethylbut-2-enyl, (Z)-2-ethylbut-2-enyl, (E)-1-ethylbut-2-enyl, (Z)-1-ethylbut-2-enyl, (E)-3-ethylbut-1-enyl, (Z)-3-ethylbut-1-enyl, 2-ethylbut-1-enyl, (E)-1-ethylbut-1-enyl, (Z)-1-ethylbut-1-enyl, 2-propylprop-2-enyl, 1-propylprop-2-enyl, 2-isopropylprop-2-enyl, 1-isopropylprop-2-enyl, (E)-2-propylprop-1-enyl, (Z)-2-propylprop-1-enyl, (E)-1-propylprop-1-enyl, (Z)-1-propylprop-1-enyl, (E)-2-isopropylprop-1-enyl, (Z)-2-isopropylprop-1-enyl, (E)-1-isopropylprop-1-enyl, (Z)-1-isopropylprop-1-enyl, 1-(1,1-dimethylethyl)ethenyl, buta-1,3-dienyl, penta-1,4-dienyl, hexa-1,5-dienyl or methylhexadienyl. Particularly, said group is vinyl or allyl. This definition also applies to alkenyl as part of a composite substituent unless defined elsewhere.

Alkynyl: straight-chain or branched hydrocarbyl substituents having 2 to 8, preferably 2 to 6, and more preferably 2 to 4 carbon atoms and one triple bond in any position, for example (but not limited to) $C_2$-$C_6$-alkynyl, such as ethynyl, prop-1-ynyl, prop-2-ynyl, but-1-ynyl, but-2-ynyl, but-3-ynyl, 1-methylprop-2-ynyl, pent-1-ynyl, pent-2-ynyl, pent-3-ynyl, pent-4-ynyl, 2-methylbut-3-ynyl, 1-methylbut-3-ynyl, 1-methylbut-2-ynyl, 3-methylbut-1-ynyl, 1-ethylprop-2-ynyl, hex-1-ynyl, hex-2-ynyl, hex-3-ynyl, hex-4-ynyl, hex-5-ynyl, 3-methylpent-4-ynyl, 2-methylpent-4-ynyl, 1-methylpent-4-ynyl, 2-methylpent-3-ynyl, 1-methylpent-3-ynyl, 4-methylpent-2-ynyl, 1-methylpent-2-ynyl, 4-methylpent-1-ynyl, 3-methylpent-1-ynyl, 2-ethylbut-3-ynyl, 1-ethylbut-3-ynyl, 1-ethylbut-2-ynyl, 1-propylprop-2-ynyl, 1-isopropylprop-2-ynyl, 2,2-dimethylbut-3-ynyl, 1,1-dimethylbut-3-ynyl, 1,1-dimethylbut-2-ynyl, or 3,3-dimethylbut-1-ynyl group. Particularly, said alkynyl group is ethynyl, prop-1-ynyl, or prop-2-ynyl. This definition also applies to alkynyl as part of a composite substituent unless defined elsewhere.

Alkylamino: monoalkylamino or dialkylamino, wherein monoalkylamino represents an amino radical having one alkyl residue with 1 to 4 carbon atoms attached to the nitrogen atom. Non-limiting examples include methylamino, ethylamino, n-propylamino, isopropylamino, n-butylamino and tert-butylamino. Wherein dialkylamino represents an amino radical having two independently selected alkyl residues with 1 to 4 carbon atoms each attached to the nitrogen atom. Non-limiting examples include N,N-dimethylamino, N,N-diethyl-amino, N,N-diisopropylamino, N-ethyl-N-methylamino, N-methyl-N-n-propylamino, N-isopropyl-N-n-propylamino and N-tert-butyl-N-methylamino.

Alkoxy: saturated, straight-chain or branched alkoxy substituents having 1 to 6, more preferably 1 to 4 carbon atoms, for example (but not limited to) $C_1$-$C_6$-alkoxy such as methoxy, ethoxy, propoxy, 1-methylethoxy, butoxy, 1-methylpropoxy, 2-methylpropoxy, 1,1-dimethylethoxy, pentoxy, 1-methylbutoxy, 2-methylbutoxy, 3-methylbutoxy, 2,2-dimethylpropoxy, 1-ethylpropoxy, 1,1-dimethylpropoxy, 1,2-dimethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy. This definition also applies to alkoxy as part of a composite substituent unless defined elsewhere.

Cycloalkyl: mono- or polycyclic, saturated hydrocarbyl substituents having 3 to 12, preferably 3 to 8 and more preferably 3 to 6 carbon ring members, for example (but not limited to) cyclopropyl, cyclopentyl, cyclohexyl and adamantyl. This definition also applies to cycloalkyl as part of a composite substituent, for example $C_3$-$C_6$-cycloalkyl-$C_1$-$C_4$-alkyl, unless defined elsewhere.

Haloalkyl: straight-chain or branched alkyl substituents having 1 to 6, preferably 1 to 4 carbon atoms (as specified above), in which some or all of the hydrogen atoms in these groups are replaced by halogen atoms as specified above, for example (but not limited to) $C_1$-$C_3$-haloalkyl such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and 1,1,1-trifluoroprop-2-yl. This definition also applies to haloalkyl as part of a composite substituent unless defined elsewhere.

Haloalkenyl and haloalkynyl are defined analogously to haloalkyl except that, instead of alkyl groups, alkenyl and alkynyl groups are present as part of the substituent.

Haloalkoxy: straight-chain or branched alkoxy substituents having 1 to 6, preferably 1 to 4 carbon atoms (as specified above), in which some or all of the hydrogen atoms in these groups are replaced by halogen atoms as specified above, for example (but not limited to) $C_1$-$C_3$-haloalkoxy such as chloromethoxy, bromomethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy and 1,1,1-trifluoroprop-2-oxy. This definition also applies to haloalkoxy as part of a composite substituent, unless defined elsewhere.

Aryl: mono-, bi- or tricyclic aromatic or partially aromatic substituents having 6 to 14 carbon atoms, for example (but not limited to) phenyl, naphthyl, tetrahydronapthyl, indenyl and indanyl. The binding to the superordinate general structure can be carried out via any possible ring member of the aryl residue. Aryl is preferably selected from phenyl, 1-naphthyl, 2-naphthyl, 9-phenantryl und 9-antracenyl. Phenyl is particularly preferred.

The term "enantioselective" as used herein means that one of the two possible enantiomers of the hydrogenation product, namely the enantiomer of the formula (Ia) or the enantiomer of the formula (Ib), is preferably formed. The "enantiomeric excess" or "ee" indicates the degree of enantioselectivity:

$$\%\ ee = \frac{\text{major enantiomer (mol)} - \text{minor enantiomer (mol)}}{\text{major enantiomer (mol)} + \text{minor enantiomer (mol)}} \times 100\%$$

The major enantiomer can be controlled by the selection of the chiral ligand, for example by selecting the chiral ligand of the formula (IIIa) or the opposite enantiomer (the ligand of the formula (IIIb)), or respectively by selecting the chiral ligand of the formula (IVa) or the opposite enantiomer (the ligand of the formula (IVb)).

The process according to the invention is used for preparing the compound of the formula (Ta) or (Ib), preferably (Ia).

Preferred are compounds of the formula (Ia) or (Ib), in particular (Ia), wherein the substituents are defined as follows:

$R^1$ is $C_1$-$C_6$-alkyl or $C_6$-$C_{14}$-aryl-$C_1$-$C_4$-alkyl,
 wherein $C_6$-$C_{14}$-aryl in the $C_6$-$C_{14}$-aryl-$C_1$-$C_4$-alkyl moiety is unsubstituted or substituted by one to five substituents selected from the group consisting of halogen, $C_1$-$C_4$-alkyl, $C_1$-$C_4$-haloalkyl, $C_1$-$C_4$-alkoxy and $C_1$-$C_4$-haloalkoxy
$R^2$ and $R^3$ are the same and are selected from $C_1$-$C_4$-alkyl,
$R^4$ is $C_1$-$C_4$-alkyl, $C_1$-$C_4$-haloalkyl, $C_1$-$C_4$-alkoxy, $C_1$-$C_4$-haloalkoxy, phenyl or benzyl,
n is 0, 1 or 2,
each substituent $R^5$, if present, is independently selected from the group consisting of halogen, $C_1$-$C_6$-alkyl and $C_1$-$C_6$-haloalkyl.

More preferred are compounds of the formula (Ia) or (Ib), in particular (Ia), wherein the substituents are defined as follows:

$R^1$ is $C_1$-$C_6$-alkyl
$R^2$ and $R^3$ are the same and are selected from $C_1$-$C_4$-alkyl,
$R^4$ is $C_1$-$C_4$-alkyl, $C_1$-$C_4$-haloalkyl, phenyl or benzyl,
n is 0, 1 or 2,
each substituent $R^5$, if present, is independently selected from the group consisting of halogen and $C_1$-$C_6$-alkyl.

Even more preferred are compounds of the formula (Ia) or (Ib), in particular (Ia), wherein the substituents are defined as follows:

$R^1$ is methyl, ethyl or n-propyl,
$R^2$ and $R^3$ are methyl,
$R^4$ is $C_1$-$C_4$-alkyl,
n is 0, 1 or 2,
each substituent $R^5$, if present, is independently selected from the group consisting of halogen and $C_1$-$C_6$-alkyl.

Most preferred are compounds of the formula (Ia) or (Ib), in particular (Ia), wherein the substituents are defined as follows:

$R^1$ is methyl or n-propyl,
$R^2$ and $R^3$ are methyl,
$R^4$ is methyl,
n is 0 or 1,
substituent $R^5$, if present, is fluorine.

The process according to the invention comprises enantioselective hydrogenation of the compound of the formula (II). The substituents $R^1$, $R^2$, $R^3$, $R^4$, $R^5$ and the integer n in the compound of the formula (II) are each as defined for the compound of the formula (Ta) or (Ib).

The enantioselective hydrogenation of the compound of the formula (II) is conducted in presence of an additive selected from the group consisting of Brønsted acids, Lewis acids, and mixtures thereof.

In a preferred embodiment of the process according to the invention, the additive is selected from the group consisting of hexafluorophosphoric acid, acetic acid, trifluoromethylsulfonic acid, water, pentafluorophenol, 3,5-bis(trifluoromethyl)phenol, tetrafluoroboric acid, tetrafluoroboric acid diethylether complex, nafion, amberlyst, 1,1,1,3,3,3-hexafluoro-2-(trifluoromethyl)propan-2-ol, triphenylborane, tris[3,5-bis(trifluoro-methyl)phenyl]borane, tris(2,3,4,5,6-pentafluorophenyl)borane, borane tetrahydrofurane complex, boric acid, aluminum (III) trifluoromethanesulfonate, zinc (II) trifluoromethanesulfonate, scandium (III) trifluoromethanesulfonate, aluminum (III) fluoride, titanium (IV) isopropoxide, trimethyl aluminum, boron trifluoride, complexes of boron trifluoride, and mixtures thereof.

Suitable complexes of boron trifluoride are complexes of boron trifluoride with organic solvents, such as dialkyl ethers or alcohols, and complexes of boron trifluoride with organic acids, such as carboxylic acids. Preferred boron trifluoride complexes are selected from the group consisting of boron trifluoride-diethylether complex, boron trifluoride acetic acid complex and boron trifluoride n-propanol complex.

In a more preferred embodiment of the process according to the invention, the additive is selected from the group consisting of hexafluorophosphoric acid, pentafluorophenol, 3,5-bis(trifluoromethyl)phenol, tetrafluoroboric acid diethylether complex, triphenylborane, tris[3,5-bis(trifluoromethyl)phenyl]borane, tris(2,3,4,5,6-pentafluorophenyl)borane, aluminum (III) trifluoromethanesulfonate, scandium (III) trifluoromethanesulfonate, aluminum (III) fluoride, titanium (IV) isopropoxide, trimethyl aluminum, boron trifluoride, complexes of boron trifluoride, and mixtures thereof, wherein the boron trifluoride complexes are preferably selected from the group consisting of boron trifluoride-diethylether complex, boron trifluoride acetic acid complex and boron trifluoride n-propanol complex.

In a even more preferred embodiment of the process according to the invention, the additive is selected from the group consisting of hexafluorophosphoric acid, pentafluorophenol, 3,5-bis(trifluoromethyl)phenol, triphenylborane, tris[3,5-bis(trifluoromethyl)phenyl]borane, tris(2,3,4,5,6-pentafluorophenyl)borane, aluminum (III) trifluoromethanesulfonate, scandium (III) trifluoromethanesulfonate, aluminum (III) fluoride, titanium (IV) isopropoxide, trimethyl aluminum, boron trifluoride, complexes of boron trifluoride, and mixtures thereof, wherein the boron trifluoride complexes are preferably selected from the group consisting of boron trifluoride-diethylether complex, boron trifluoride acetic acid complex and boron trifluoride n-propanol complex.

In the most preferred embodiment of the process according to the invention, the additive is selected from the group consisting of aluminum (III) trifluoromethanesulfonate, scandium (III) trifluoromethanesulfonate, tris(2,3,4,5,6-pentafluorophenyl)borane, hexafluorophosphoric acid, boron trifluoride, boron trifluoride-diethylether complex, boron trifluoride acetic acid complex and boron trifluoride n-propanol complex.

The amount of additive selected from the group consisting of Brønsted acids and Lewis acids used is preferably within the range of from 0.1 mol % to 10 mol %, more preferably 0.2 mol % to 5 mol %, most preferably 0.3 mol % to 2 mol %, in particular 0.4 mol % to 1 mol %, based on the amount of the compound of the formula (II).

The enantioselective hydrogenation of the compound of the formula (II) is conducted in presence of a chiral iridium catalyst comprising a chiral ligand of the formula (IIIa), (IIIb), (IVa) or (IVb).

In a preferred embodiment of the process according to the invention, the substituents of formulae (Ia), (Ib), (II), (IIIa), (IIIb), (IVa), (IVb), (Ixa) and (Ixb) are defined as follows:

$R^1$ is $C_1$-$C_6$-alkyl or $C_6$-$C_{14}$-aryl-$C_1$-$C_4$-alkyl,
- wherein $C_6$-$C_{14}$-aryl in the $C_6$-$C_{14}$-aryl-$C_1$-$C_4$-alkyl moiety is unsubstituted or substituted by one to five substituents selected from the group consisting of halogen, $C_1$-$C_4$-alkyl, $C_1$-$C_4$-haloalkyl, $C_1$-$C_4$-alkoxy and $C_1$-$C_4$-haloalkoxy $R^2$ and $R^3$ are the same and are selected from $C_1$-$C_4$-alkyl, $R^4$ is $C_1$-$C_4$-alkyl, $C_1$-$C_4$-haloalkyl, $C_1$-$C_4$-alkoxy, $C_1$-$C_4$-haloalkoxy, phenyl or benzyl, n is 0, 1 or 2, each substituent $R^5$, if present, is independently selected from the group consisting of halogen, $C_1$-$C_6$-alkyl and $C_1$-$C_6$-haloalkyl, $R^6$ is $C_1$-$C_6$-alkyl, $C_1$-$C_6$-haloalkyl, $C_3$-$C_7$-cycloalkyl or $C_6$-$C_{14}$-aryl,
- wherein the $C_6$-$C_{14}$-aryl is unsubstituted or substituted by one to five substituents selected from the group consisting of halogen, $C_1$-$C_4$-alkyl, $C_1$-$C_4$-haloalkyl, $C_1$-$C_4$-alkoxy, $C_1$-$C_4$-haloalkoxy and phenyl, wherein the phenyl again is unsubstituted or substituted by one to five $C_1$-$C_6$-alkyl substituents, $R^7$ and $R^8$ are independently from one another hydrogen selected from the group consisting of hydrogen, $C_1$-$C_6$-alkyl, $C_6$-$C_{14}$-aryl, $C_1$-$C_6$-alkoxy or $C_1$-$C_6$-haloalkyl,
- wherein the $C_6$-$C_{14}$-aryl is unsubstituted or substituted by one to five $C_1$-$C_4$-alkyl substituents, $R^9$ and $R^{10}$ are independently from one another selected from the group consisting of $C_1$-$C_6$-alkyl, $C_1$-$C_6$-alkoxy, di($C_1$-$C_6$-alkyl)amino, $C_3$-$C_{12}$-cycloalkyl, $C_6$-$C_{14}$-aryl, $C_6$-$C_{14}$-aryloxy and $C_6$-$C_{14}$-aryl-$C_1$-$C_4$-alkyl,
- wherein the $C_1$-$C_6$-alkyl, $C_1$-$C_6$-alkoxy and di($C_1$-$C_6$-alkyl)amino moieties are optionally substituted by 1 to 3 substituents independently selected from the group consisting of halogen, $C_1$-$C_4$-alkoxy, $C_1$-$C_4$-haloalkyl, $C_1$-$C_4$-haloalkoxy and phenyl, wherein the phenyl may be substituted by one to five substituents selected independently from each other from halogen, $C_1$-$C_4$-alkyl, $C_1$-$C_4$-alkoxy, $C_1$-$C_4$-haloalkyl, and $C_1$-$C_4$-haloalkoxy, and
- wherein the $C_6$-$C_{14}$-aryl, $C_6$-$C_{14}$-aryloxy and $C_3$-$C_{12}$-cycloalkyl, as such or as part of a composite substituent, in each case is unsubstituted or substituted by one to five substituents selected from the group consisting of halogen, $C_1$-$C_4$-alkyl, $C_1$-$C_4$-haloalkyl, $C_1$-$C_4$-alkoxy, $C_1$-$C_4$-haloalkoxy and phenyl, wherein the phenyl is unsubstituted or substituted by one to five $C_1$-$C_6$-alkyl substituents or $R^9$ and $R^{10}$ together with the phosphorus atom which they are bound to, form a phospholane ring, which may be substituted with one or two $C_1$-$C_6$-alkyl groups, m is 1 or 2, A is $A^1$ = 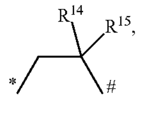

in which the bond identified by "*" is bound directly to the phosphorus atom and in which the bond identified by "#" is bound directly to the oxazoline moiety, $R^{13}$ is $C_3$-$C_6$-alkyl, $C_3$-$C_{12}$-cycloalkyl, $C_6$-$C_{14}$-aryl or $C_6$-$C_{14}$-aryl-$C_1$-$C_4$-alkyl, wherein the $C_6$-$C_{14}$-aryl and the $C_6$-$C_{14}$-aryl in the $C_6$-$C_{14}$-aryl-$C_1$-$C_4$-alkyl moiety in each case is unsubstituted or substituted by one to five substituents selected from the group consisting of halogen, $C_1$-$C_4$-alkyl, $C_1$-$C_4$-haloalkyl, $C_1$-$C_4$-alkoxy and $C_1$-$C_4$-haloalkoxy, $R^{14}$ and $R^{15}$ are independently from one another selected from the group consisting of $C_1$-$C_6$-alkyl, $C_3$-$C_{12}$-cycloalkyl, $C_6$-$C_{14}$-aryl and $C_6$-$C_{14}$-aryl-$C_1$-$C_4$-alkyl, wherein the $C_6$-$C_{14}$-aryl and the $C_6$-$C_{14}$-aryl in the $C_6$-$C_{14}$-aryl-$C_1$-$C_4$-alkyl moiety is unsubstituted or substituted by one to five substituents selected from the group consisting of halogen, $C_1$-$C_4$-alkyl, $C_1$-$C_4$-haloalkyl, $C_1$-$C_4$-alkoxy and $C_1$-$C_4$-haloalkoxy, or $R^{14}$ and $R^{15}$ together with the carbon which they are bound to, form a $C_5$-$C_6$-cycloalkyl ring, $R^{16}$ and $R^{17}$ are independently from one another selected from the group consisting of $C_1$-$C_6$-alkyl, $C_3$-$C_{12}$-cycloalkyl, $C_6$-$C_{14}$-aryl and $C_6$-$C_{14}$-aryl-$C_1$-$C_4$-alkyl, wherein the $C_1$-$C_6$-alkyl is optionally substituted by 1 to 3 substituents independently selected from the group consisting of halogen, $C_1$-$C_4$-alkoxy, $C_1$-$C_4$-haloalkyl, $C_1$-$C_4$-haloalkoxy and phenyl, wherein the phenyl may be substituted by one to five substituents selected independently from each other from halogen, $C_1$-$C_4$-alkyl, phenyl, $C_1$-$C_4$-alkoxy, $C_1$-$C_4$-haloalkyl, and $C_1$-$C_4$-haloalkoxy, and wherein the $C_6$-$C_{14}$-aryl and the $C_6$-$C_{14}$-aryl in the $C_6$-$C_{14}$-aryl-$C_1$-$C_4$-alkyl moiety in each case is unsubstituted or substituted by one to five substituents selected from the group consisting of halogen, $C_1$-$C_4$-alkyl, $C_1$-$C_4$-haloalkyl, $C_1$-$C_4$-alkoxy and $C_1$-$C_4$-haloalkoxy, or $R^{16}$ and $R^{17}$ together with the phosphorus atom which they are bound to, form a phospholane ring, which may be substituted with one or two $C_1$-$C_6$-alkyl groups, $R^{19}$ is phenyl, t-butyl, $R^{20}$ is hydrogen, methyl, $R^{21}$ is benzyl, methyl, $R^{22}$ is cyclohexyl, and the additive is selected from the group consisting of hexafluorophosphoric acid, trifluoromethyl sulfonic acid, water, pentafluorophenol, 3,5-bis(trifluoromethyl) phenol, tetrafluoroboric acid, tetrafluoroboric acid diethylether complex, nafion, amberlyst, 1,1,1,3,3,3-hexafluoro-2-(trifluoromethyl)propan-2-ol, triphenylborane, tris[3,5-bis(trifluoromethyl)phenyl]borane, tris (2,3,4,5,6-pentafluorophenyl)borane, borane tetrahydrofurane complex, boric acid, aluminum (III) trifluoromethanesulfonate, zinc (II) trifluoromethanesulfonate, scandium (III) trifluoromethanesulfonate, aluminum (III) fluoride, titanium (IV) isopropoxide, trimethyl aluminum, boron trifluoride, complexes of boron trifluoride, and mixtures thereof, wherein the boron trifluoride complexes are preferably selected from the group consisting of boron trifluoride-diethylether complex, boron trifluoride acetic acid complex and boron trifluoride n-propanol complex.

In a more preferred embodiment of the process according to the invention, the substituents of formulae (Ia), (Ib), (II), (IIIa), (IIIb), (IVa), (IVb), (IXa), and (IXb) are defined as follows:

$R^1$ is $C_1$-$C_6$-alkyl, $R^2$ and $R^3$ are the same and are selected from $C_1$-$C_4$-alkyl, $R^4$ is $C_1$-$C_4$-alkyl, $C_1$-$C_4$-haloalkyl, $C_1$-$C_4$-alkoxy, $C_1$-$C_4$-haloalkoxy, phenyl or benzyl, n is 0, 1 or 2, each substituent $R^5$, if present, is independently selected from the group consisting of halogen, $C_1$-$C_6$-alkyl and $C_1$-$C_6$-haloalkyl, $R^6$ is selected from the group consisting of 1-naphtyl, 2-naphtyl, 9-antracenyl, 9-phenantryl or phenyl, which is unsubstituted or substituted by one to five substituents selected from the group consisting of halogen, $C_1$-$C_4$-alkoxy, $C_1$-$C_4$-alkyl, $C_1$-$C_4$-haloalkyl and phenyl, wherein the phenyl again is unsubstituted or substituted by one to five $C_1$-$C_6$-alkyl substituents, $R^7$ and $R^8$ are independently from one another hydrogen or $C_1$-$C_6$-alkyl, $R^9$ and $R^{10}$ are independently from one another selected from the group consisting of ethyl, iso-propyl, sec-butyl, iso-butyl, tert-butyl, cyclohexyl, cyclopentyl, adamantyl and benzyl, and m is 1 or 2, A is $A^1$ =

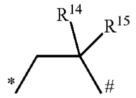

in which the bond identified by "*" is bound directly to the phosphorus atom and in which the bond identified by "#" is bound directly to the oxazoline moiety, $R^{13}$ is tert-butyl, iso-propyl or phenyl, $R^{14}$ and $R^{15}$ are methyl, $R^{16}$ and $R^{17}$ are each the same and 2-methylphenyl or 3,5-bismethylphenyl, and the additive is selected from the group consisting of aluminum (III) trifluoromethanesulfonate, scandium (III) trifluoromethanesulfonate, tris(2,3,4,5,6-pentafluorophenyl)borane, hexafluorophosphoric acid, boron trifluoride and complexes of boron trifluoride, wherein the complexes of boron trifluoride are preferably selected from boron trifluoride-diethylether complex, boron trifluoride acetic acid complex and boron trifluoride n-propanol complex, $R^{19}$ is phenyl, $R^{20}$ is methyl, $R^{21}$ is benzyl, $R^{22}$ is cyclohexyl, and the additive is selected from the group consisting of hexafluorophosphoric acid, pentafluorophenol, 3,5-bis (trifluoromethyl)phenol, triphenylborane, tris[3,5-bis (trifluoromethyl)phenyl]borane, tris(2,3,4,5,6-pentafluorophenyl)borane, aluminum (III) trifluoromethanesulfonate, scandium (III) trifluoromethanesulfonate, aluminum (III) fluoride, titanium (IV) isopropoxide, trimethyl aluminum, boron trifluoride, complexes of boron trifluoride, and mixtures thereof, wherein the complexes of boron trifluoride are preferably selected from boron trifluoride-diethylether complex, boron trifluoride acetic acid complex and boron trifluoride n-propanol complex.

In the most preferred embodiment of the process according to the invention, the substituents of formulae (Ia), (Ib), (II), (IIIa), (IIIb) are defined as follows:

$R^1$ is $C_1$-$C_4$-alkyl, $R^2$ and $R^3$ are methyl, $R^4$ is $C_1$-$C_4$-alkyl, n is 0 or 1

$R^5$ if present, is fluorine, $R^6$ phenyl, 2,6- or 3,5-dimethylphenyl, 2,4,6-trimethylphenyl, 4-tert-butylphenyl, 4-methoxyphenyl, 3,5-bis-tert-butyl-4-methoxyphenyl, 4-tert-butyl-2,6-dimethylphenyl, 4-fluorophenyl, 4-trifluoromehtylphenyl, 1-naphtyl, 9-antracenyl 2,4,6-triisopropylphenyl, 9-phenantryl or 2,6-diethyl-4-methylphenyl, $R^7$ is hydrogen, $R^8$ is hydrogen or methyl, $R^9$ and $R^{10}$ are each the same and selected from the group consisting of ethyl, iso-propyl, tert-butyl, cyclopentyl, adamantyl and cyclohexyl, m is 1.

In a preferred embodiment of the process according to the invention, the ligand of the formula (IIIa) or (IIIb) is used. Depending on whether compound (Ia) or (Ib) is the desired product, the ligand of the formula (IIIa) or (IIIb) is selected.

Preferred are ligands of the formulae (IIIa) and (IIIb), wherein the substituents are defined as follows:

$R^6$ is $C_1$-$C_6$-alkyl, $C_1$-$C_6$-haloalkyl, $C_3$-$C_7$-cycloalkyl or $C_6$-$C_{14}$-aryl, wherein the $C_6$-$C_{14}$-aryl is unsubstituted or substituted by one to five substituents selected from the group consisting of halogen, $C_1$-$C_4$-alkyl, $C_1$-$C_4$-haloalkyl, $C_1$-$C_4$-alkoxy, $C_1$-$C_4$-haloalkoxy and phenyl, wherein the phenyl again is unsubstituted or substituted by one to five $C_1$-$C_6$-alkyl substituents, $R^7$ and $R^8$ are independently from one another selected from the group consisting of hydrogen, $C_1$-$C_6$-alkyl, $C_1$-$C_6$-alkoxy, $C_6$-$C_{14}$-aryl or $C_1$-$C_6$-haloalkyl, wherein the $C_6$-$C_{14}$-aryl is unsubstituted or substituted by one to five $C_1$-$C_4$-alkyl substituents, $R^9$ and $R^{10}$ are independently from one another selected from the group consisting of $C_1$-$C_6$-alkyl, $C_1$-$C_6$-alkoxy, di($C_1$-$C_6$-alkyl)amino, $C_3$-$C_{12}$-cycloalkyl, $C_6$-$C_{14}$-aryl, $C_6$-$C_{14}$-aryloxy and $C_6$-$C_{14}$-aryl-$C_1$-$C_4$-alkyl, wherein the $C_1$-$C_6$-alkyl, $C_1$-$C_6$-alkoxy and di($C_1$-$C_6$-alkyl)amino moieties are optionally substituted by 1 to 3 substituents independently selected from the group consisting of halogen, $C_1$-$C_4$-alkoxy, $C_1$-$C_4$-haloalkyl, $C_1$-$C_4$-haloalkoxy and phenyl, wherein the phenyl may be substituted by one to five substituents selected independently from each other from halogen, $C_1$-$C_4$-alkyl, $C_1$-$C_4$-alkoxy, $C_1$-$C_4$-haloalkyl, and $C_1$-$C_4$-haloalkoxy, and wherein the $C_6$-$C_{14}$-aryloxy, $C_3$-$C_{12}$-cycloalkyl and $C_6$-$C_{14}$-aryl, as such or as part of a composite substituent, in each case is unsubstituted or substituted by one to five substituents selected from the group consisting of halogen, $C_1$-$C_4$-alkyl, $C_1$-$C_4$-haloalkyl, $C_1$-$C_4$-alkoxy, $C_1$-$C_4$-haloalkoxy and phenyl, wherein the phenyl is unsubstituted or substituted by one to five $C_1$-$C_6$-alkyl substituents or $R^9$ and $R^{10}$ together with the phosphorus atom which they are bound to, form a phospholane ring, which may be substituted with one or two $C_1$-$C_6$-alkyl groups, and m is 1 or 2.

More preferred are ligands of the formulae (IIIa) and (IIIb), wherein the substituents are defined as follows:

$R^6$ is selected from the group consisting of 1-naphtyl, 2-naphtyl, 9-antracenyl, 9-phenantryl or phenyl, which is unsubstituted or substituted by one to five substituents selected from the group consisting of halogen, $C_1$-$C_4$-alkoxy, $C_1$-$C_4$-alkyl, $C_1$-$C_4$-haloalkyl and phenyl, wherein the phenyl again is unsubstituted or substituted by one to five $C_1$-$C_6$-alkyl substituents, $R^7$ and $R^8$ are independently from one another hydrogen or $C_1$-$C_6$-alkyl, $R^9$ and $R^{10}$ are independently from one another selected from the group consisting of ethyl, iso-propyl, sec-butyl, iso-butyl, tert-butyl, cyclohexyl, cyclopentyl, adamantyl and benzyl, and m is 1 or 2.

Most preferred are ligands of the formulae (IIIa) and (IIIb), wherein the substituents are defined as follows:

$R^6$ is selected from the group consisting of, phenyl, 2,6- or 3,5-dimethylphenyl, 2,4,6-trimethylphenyl, 4-tert-butylphenyl, 4-methoxyphenyl, 3,5-bis-tert-butyl-4-methoxyphenyl, 4-tert-butyl-2,6-dimethylphenyl, 4-fluorophenyl, 4-trifluoromehtylphenyl, 1-naphtyl, 9-antracenyl 2,4,6-triisopropylphenyl, 9-phenantryl or 2,6-diethyl-4-methylphenyl, $R^7$ is hydrogen $R^8$ is hydrogen or methyl, $R^9$ and $R^{10}$ are each the same and tert-butyl, cyclopentyl or cyclohexyl, and m is 1.

In another preferred embodiment of the process according to the invention, the ligand of the formula (IVa) or (IVb) is used. Depending on whether compound (Ia) or (Ib) is the desired product, the ligand of the formula (IVa) or (IVb) is selected.

Preferred are ligands of the formulae (IVa) and (IVb), wherein the substituents are defined as follows:

A is $A^1$ = 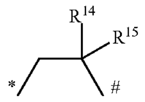 , in which the bond identified by "*" is bound directly to the phosphorus atom and in which the bond identified by "#" is bound directly to the oxazoline moiety, $R^{13}$ is $C_3$-$C_6$-alkyl, $C_3$-$C_{12}$-cycloalkyl, $C_6$-$C_{14}$-aryl or $C_6$-$C_{14}$-aryl-$C_1$-$C_4$-alkyl, wherein the $C_6$-$C_{14}$-aryl and the $C_6$-$C_{14}$-aryl in the $C_6$-$C_{14}$-aryl-$C_1$-$C_4$-alkyl moiety in each case is unsubstituted or substituted by one to five substituents selected from the group consisting of halogen, $C_1$-$C_4$-alkyl, $C_1$-$C_4$-haloalkyl, $C_1$-$C_4$-alkoxy and $C_1$-$C_4$-haloalkoxy, $R^{14}$ and $R^{15}$ are independently from one another selected from the group consisting of $C_1$-$C_6$-alkyl, $C_6$-$C_{14}$-aryl, $C_3$-$C_{12}$-cycloalkyl, and $C_6$-$C_{14}$-aryl-$C_1$-$C_4$-alkyl, wherein $C_6$-$C_{14}$-aryl and the $C_6$-$C_{14}$-aryl in the $C_6$-$C_{14}$-aryl-$C_1$-$C_4$-alkyl moiety is unsubstituted or substituted by one to five substituents selected from the group consisting of halogen, $C_1$-$C_4$-alkyl, $C_1$-$C_4$-haloalkyl, $C_1$-$C_4$-alkoxy and $C_1$-$C_4$-haloalkoxy, or $R^{14}$ and $R^{15}$ together with the carbon which they are bound to, form a $C_5$-$C_6$-cycloalkyl ring, $R^{16}$ and $R^{17}$ are independently from one another selected from the group consisting of $C_1$-$C_6$-alkyl, $C_3$-$C_{12}$-cycloalkyl, $C_6$-$C_{14}$-aryl and $C_6$-$C_{14}$-aryl-$C_1$-$C_4$-alkyl, wherein the $C_1$-$C_6$-alkyl is optionally substituted by 1 to 3 substituents independently selected from the group consisting of halogen, $C_1$-$C_4$-alkoxy, $C_1$-$C_4$-haloalkyl, $C_1$-$C_4$-haloalkoxy and phenyl, wherein the phenyl may be substituted by one to five substituents selected independently from each other from halogen, $C_1$-$C_4$-alkyl, $C_1$-$C_4$-alkoxy, $C_1$-$C_4$-haloalkyl, and $C_1$-$C_4$-haloalkoxy, and wherein the $C_6$-$C_{14}$-aryl and the $C_6$-$C_{14}$-aryl in the $C_6$-$C_{14}$-aryl-$C_1$-$C_4$-alkyl moiety in each case is unsubstituted or substituted by one to five substituents selected from the group consisting of halogen, $C_1$-$C_4$-alkyl, phenyl, $C_1$-$C_4$-haloalkyl, $C_1$-$C_4$-alkoxy and $C_1$-$C_4$-haloalkoxy, or $R^{16}$ and $R^{17}$ together with the phosphorus atom which they are bound to, form a phospholane ring, which may be substituted with one or two $C_1$-$C_6$-alkyl groups.

More preferred are ligands of the formulae (IVa) and (IVb), wherein the substituents are defined as follows:

A is

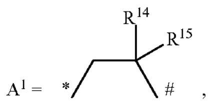

in which the bond identified by "*" is bound directly to the phosphorus atom and in which the bond identified by "#" is bound directly to the oxazoline moiety, $R^{13}$ is iso-propyl, sec-butyl, iso-butyl, tert-butyl, phenyl or benzyl, $R^{14}$ and $R^{15}$ are independently from one another selected from the group consisting of $C_1$-$C_6$-alkyl, and $C_6$-aryl-$C_1$-$C_4$-alkyl, wherein the $C_6$-aryl in the $C_6$-$C_{14}$-aryl-$C_1$-$C_4$-alkyl moiety is unsubstituted or substituted by one to five substituents selected from the group consisting of halogen and $C_1$-$C_4$-alkyl, $R^{16}$ and $R^{17}$ are independently from one another phenyl, 1-naphthyl or 2-naphthyl, which in each case is unsubstituted or substituted by one to five $C_1$-$C_4$-alkyl substituents Most preferred are ligands of the formulae (IVa) and (IVb), wherein the substituents are defined as follows:

A is

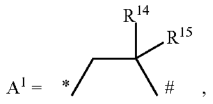

In which the bond identified by "*" is bound directly to the phosphorus atom and in which the bond identified by "#" is bound directly to the oxazoline moiety, $R^{13}$ is tert-butyl, $R^{14}$ and $R^{15}$ are methyl, and $R^{16}$ and $R^{17}$ are independently from one another phenyl, which is substituted by one or two methyl, in particular $R^{16}$ and $R^{17}$ are each the same and phenyl, which is substituted by one or two methyl or $R^{16}$ and $R^{17}$ are each the same and 2-methylphenyl or 3,5-dimethylphenyl.

In another preferred embodiment of the process according to the invention, the ligand of the formula (IXa) or (IXb) is used. Depending on whether compound (Ia) or (Ib) is the desired product, the ligand of the formula (IXa) or (IXb) is selected.

Preferred are ligands of the formulae (IXa) and (IXb), wherein the substituents are defined as follows:

$R^{19}$ are independently selected from phenyl, benzyl, t-butyl, isopropyl, cyclohexyl, $R^{20}$ are independently selected from hydrogen, methyl, ethyl, isopropyl, $R^{21}$ are independently selected from hydrogen, benzyl, methyl, ethyl, and $R^{22}$ are independently selected from cyclohexyl, phenyl, 2-methylphenyl, 4-methylphenyl, 2,6-dimethylphenyl, 3,5-dimethylphenyl, 2,4,6-trimethylphenyl.

More preferred are ligands of the formulae (IXa) and (IXb), wherein the substituents are defined as follows:

$R^{19}$ is phenyl, t-butyl, $R^{20}$ is hydrogen, methyl, $R^{21}$ is benzyl, methyl, and $R^{22}$ is cyclohexyl.

Most preferred are ligands of the formulae (IXa) and (IXb), wherein the substituents are defined as follows:

$R^{19}$ is phenyl, $R^{20}$ is methyl, $R^{21}$ is benzyl, and $R^{22}$ is cyclohexyl.

Preferably, the chiral iridium catalyst is selected from the group consisting of [IrL*(COD)]Y and [IrL*(nbd)]Y, wherein L* is the chiral ligand of the formulae (IIIa), (IIIb), (IVa) or (IVb), COD represents 1,5-cyclooctadiene, nbd represents norbornadiene, and Y is a non-coordinating anion selected from the group consisting of $[B(R^{18})_4]^-$, $PF_6^-$, $SbF_6^-$, $CF_3SO_3^-$, $[Al\{OC(CF_3)_3\}_4]^-$ (formula (VII)) and Δ-TRISPHAT (formula (VIII))

(VII)

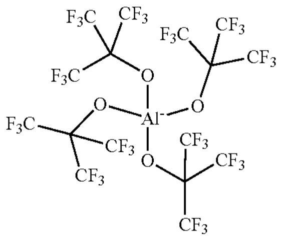

(VIII)

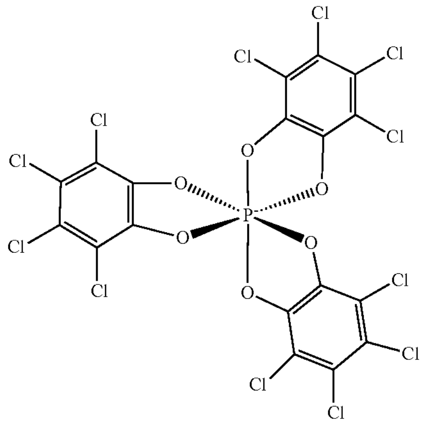

wherein $R^{18}$ is selected from fluorine and phenyl, which is unsubstituted or substituted with one to five substituents selected from $C_1$-$C_4$-alkyl, $C_1$-$C_4$-haloalkyl and halogen.

More preferred are chiral iridium catalysts of the formulae [IrL*(COD)]Y and [IrL*(nbd)]Y, wherein Y is $PF_6$, $[Al\{OC(CF_3)_3\}_4]^-$ (formula (VII)) or $[B(R^{18})_4]^-$, wherein $R^{18}$ is phenyl, which is unsubstituted or substituted with one to five substituents selected from fluorine and trifluoromethyl.

Even more preferred are chiral iridium catalysts of the general formulae (Va), (Vb), (VIa) and (VIb)

(Va)

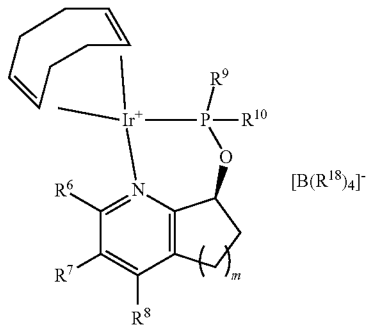

(Vb)

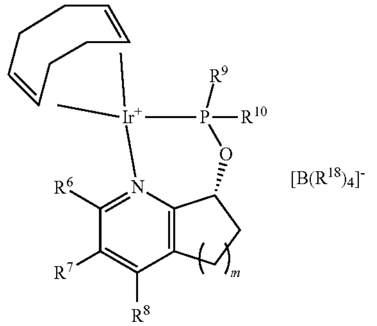

(VIa)

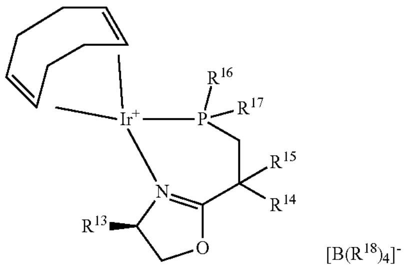

(VIb)

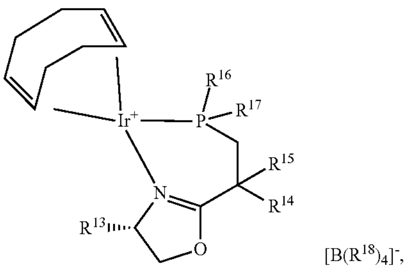

wherein $R^6$ is selected from the group consisting of 1-naphtyl, 2-naphtyl, 9-antracenyl, 9-phenantryl or phenyl, wherein 1-naphtyl, 2-naphtyl, 9-antracenyl, 9-phenantryl and phenyl are unsubstituted or substituted by one to five substituents selected from the group consisting of halogen, $C_1$-$C_4$-alkoxy, $C_1$-$C_4$-alkyl, $C_1$-$C_4$-haloalkyl and phenyl, wherein the phenyl again is unsubstituted or substituted by one to five $C_1$-$C_6$-alkyl substituents, $R^7$ and $R^8$ are independently from one another hydrogen, $C_1$-$C_6$-alkyl or $C_1$-$C_6$-alkoxy $R^9$ and $R^{10}$ are independently from one another selected from the group consisting of ethyl, iso-propyl, sec-butyl, iso-butyl, tert-butyl, cyclohexyl, cyclopentyl, adamantyl and benzyl, m is 1 or 2, $R^{13}$ is iso-propyl, sec-butyl, iso-butyl, tert-butyl, phenyl or benzyl, $R^{14}$ and $R^{15}$ are independently from one another selected from the group consisting of $C_1$-$C_6$-alkyl, and $C_6$-aryl-$C_1$-$C_4$-alkyl, wherein the $C_6$-aryl in the $C_6$-$C_{14}$-aryl-$C_1$-$C_4$-alkyl moiety is unsubstituted or substituted by one to five substituents selected from the group consisting of halogen and $C_1$-$C_4$-alkyl, $R^{16}$ and $R^{17}$ are independently from one another phenyl, 1-naphthyl or 2-naphthyl, which in each case is unsubstituted or substituted by one to five substituents selected from the group consisting of halogen, $C_1$-$C_4$-alkyl and $C_1$-$C_4$-haloalkyl, and $R^{18}$ is phenyl, which is unsubstituted or substituted with one to five substituents selected from fluorine and $C_1$-$C_4$-haloalkyl.

Particularly preferred are chiral iridium catalysts of the general formulae (Va), (Vb), (VIa) and (VIb), wherein $R^6$ is selected from the group consisting of phenyl, 2,6- or 3,5-dimethylphenyl, 2,4,6-trimethylphenyl, 4-tert-butylphenyl, 4-methoxyphenyl, 3,5-bis-tert-butyl-4-methoxyphenyl, 4-tert-butyl-2,6-dimethylphenyl, 4-fluorophenyl, 4-trifluoromehtylphenyl, 1-naphtyl, 9-antracenyl, 2,4,6-triisopropylphenyl, 9-phenantryl and 2,6-diethyl-4-methylphenyl, $R^7$ is hydrogen, $R^8$ is hydrogen or methyl $R^9$ and $R^{10}$ are each the same and tert-butyl, adamantly, cyclopentyl or cyclohexyl, m is 1, $R^{13}$ is tert-butyl, $R^{14}$ and $R^{15}$ are methyl, $R^{16}$ and $R^{17}$ are independently from one another phenyl, which is substituted by one or two methyl, in particular $R^{16}$ and $R^{17}$ are each the same and 2-methylphenyl or 3,5-dimethylphenyl, and $R^{18}$ is 3,5-bis(trifluoromethyl)phenyl.

Most preferred are chiral iridium catalysts of the general formulae (Va), (Vb), wherein $R^6$ is selected from the group consisting of phenyl, 2,6- or 3,5-dimethylphenyl, 2,4,6-trimethylphenyl, 4-tert-butylphenyl, 4-methoxyphenyl, 3,5-bis-tert-butyl-4-methoxyphenyl, 4-tert-butyl-2,6-dimethylphenyl, 4-fluorophenyl, 4-trifluoromehtylphenyl, 1-naphtyl, 9-antracenyl, 2,4,6-triisopropylphenyl, 9-phenantryl and 2,6-diethyl-4-methylphenyl, $R^7$ is hydrogen, $R^8$ is hydrogen or methyl $R^9$ and $R^{10}$ are each the same and tert-butyl, or cyclohexyl, m is 1

The amount of iridium catalyst used is preferably within the range of from 0.001 mol % to 5 mol %, more preferably 0.002 mol % to 4 mol %, most preferably 0.005 mol % to 3 mol %, in particular 0.01 mol % to 2.0 mol %, based on the amount of the compound of the formula (II).

The chiral iridium catalyst may be prepared by methods known in the art from an iridium (I) catalyst precursor, such as $[Ir(COD)Cl]_2$, the chiral ligand of the formula (IIIa), (IIIb), (IVa) or (IVb) and an alkali salt of the non-coordinating anion (S. Kaiser et al., Angew. Chem. Int. Ed. 2006, 45, 5194-5197; W. J. Drury III et al., Angew. Chem. Int. Ed. 2004, 43, 70-74).

Preferably, the process according to the invention is performed in the presence of a chiral iridium catalyst, wherein the chiral iridium catalyst is selected from the group consisting of [IrL*(COD)]Y and [IrL*(nbd)]Y, wherein L* is the chiral ligand of the formula (IIIa), (IIIb), (IVa) or (IVb), COD represents 1,5-cyclooctadiene, nbd represents norbornadiene, and Y is a non-coordinating anion selected from the group consisting of $[B(R^{18})_4]^-$, $PF_6^-$, $SbF_6^-$, $CF_3SO_3^-$, $[Al\{OC(CF_3)_3\}_4]^-$ (formula (VII)) and Δ-TRISPHAT (formula (VIII))

(VII)

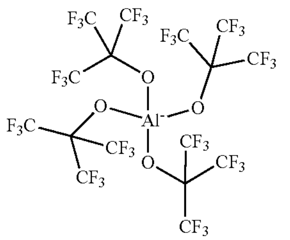

(VIII)

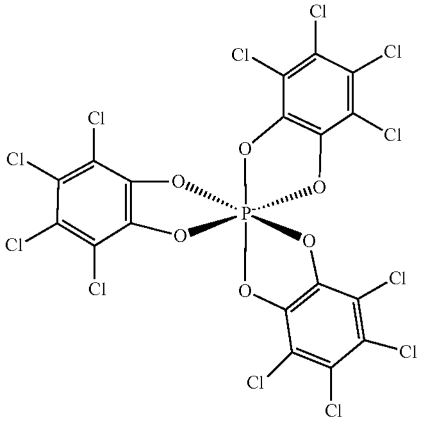

wherein $R^{18}$ is selected from fluorine and phenyl, which is unsubstituted or substituted with one to five substituents selected from $C_1$-$C_4$-alkyl, $C_1$-$C_4$-haloalkyl and halogen, and in the presence of an additive, wherein the additive is selected from the group consisting of hexafluorophosphoric acid, acetic acid, trifluoromethylsulfonic acid, water, pentafluorophenol, 3,5-bis (trifluoromethyl)phenol, tetrafluoroboric acid, tetrafluoroboric acid diethylether complex, nafion, amberlyst, 1,1,1,3,3,3-hexafluoro-2-(trifluoromethyl) propan-2-ol, triphenylborane, tris[3,5-bis(trifluoromethyl)phenyl]borane, tris(2,3,4,5,6-pentafluorophenyl) borane, borane tetrahydrofurane complex, boric acid, aluminum (III) trifluoromethanesulfonate, zinc (II) trifluoromethanesulfonate, scandium (III) trifluoromethanesulfonate, aluminum (III) fluoride, titanium (IV) isopropoxide, trimethyl aluminum, boron trifluoride, complexes of boron trifluoride, and mixtures thereof, wherein the complexes of boron trifluoride are preferably selected from boron trifluoride-diethylether complex, boron trifluoride acetic acid complex and boron trifluoride n-propanol complex.

More preferably the process according to the invention is performed in the presence of a chiral iridium catalyst, wherein the chiral iridium catalyst is selected from the group consisting of chiral iridium catalyst of the formulae [IrL*(COD)]Y and [IrL*(nbd)]Y, wherein L* is the chiral ligand of the formula (IIIa), (IIIb), (IVa) or (IVb), COD represents 1,5-cyclooctadiene, nbd represents norbornadiene, and Y is $PF_6$, $[Al\{OC(CF_3)_3\}_4]$ (formula (VII)) or $[B(R^{18})_4]$, wherein $R^{18}$ is phenyl, which is unsubstituted or substituted with one to five substituents selected from fluorine and trifluoromethyl, and in the presence of an additive, wherein the additive is selected from the group consisting of hexafluorophosphoric acid, pentafluorophenol, 3,5-bis(trifluoromethyl)phenol, tetrafluoroboric acid diethylether complex, triphenylborane, tris[3,5-bis(trifluoromethyl)phenyl]borane, tris(2,3,4,5,6-pentafluorophenyl)borane, aluminum (III) trifluoromethanesulfonate, scandium (III) trifluoromethanesulfonate, aluminum (III) fluoride, titanium (IV) isopropoxide, trimethyl aluminum, boron trifluoride, complexes of boron trifluoride, and mixtures thereof, wherein the complexes of boron trifluoride are preferably selected from boron trifluoride-diethylether complex, boron trifluoride acetic acid complex and boron trifluoride n-propanol complex.

Even more preferably the process according to the invention is performed in the presence of a chiral iridium catalyst, wherein the chiral iridium catalyst is selected from the group consisting of chiral iridium catalyst of the formulae (Va), (Vb), (VIa) and (VIb)

(Va)

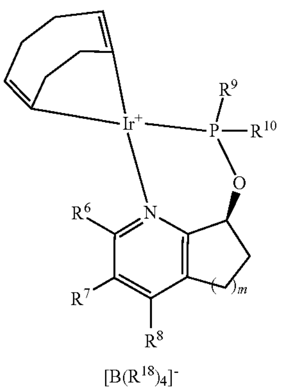

$[B(R^{18})_4]^-$

-continued (Vb)

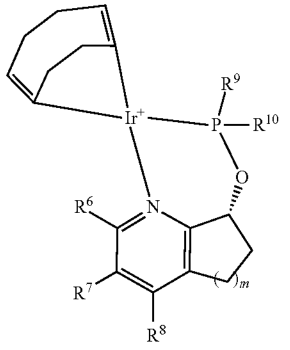

$[B(R^{18})_4]^-$ (VIa)

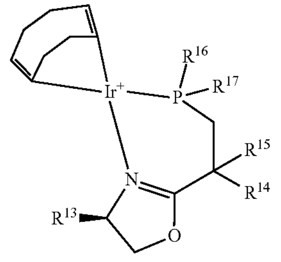

$[B(R^{18})_4]^-$ (VIb)

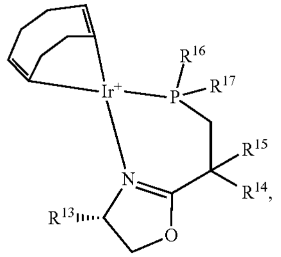

$[B(R^{18})_4]^-$ wherein $R^6$ is selected from the group consisting of 1-naphtyl, 2-naphtyl, 9-antracenyl, 9-phenantryl or phenyl, wherein 1-naphtyl, 2-naphtyl, 9-antracenyl, 9-phenantryl and phenyl are unsubstituted or substituted by one to five substituents selected from the group consisting of halogen, $C_1$-$C_4$-alkoxy, $C_1$-$C_4$-alkyl, $C_1$-$C_4$-haloalkyl and phenyl, wherein the phenyl again is unsubstituted or substituted by one to five $C_1$-$C_6$-alkyl substituents, $R^7$ and $R^8$ are independently from one another hydrogen, $C_1$-$C_6$-alkyl or $C_1$-$C_6$-alkoxy $R^9$ and $R^{10}$ are independently from one another selected from the group consisting of ethyl, iso-propyl, sec-butyl, iso-butyl, tert-butyl, cyclohexyl, cyclopentyl, adamantyl and benzyl, m is 1 or 2, $R^{13}$ is iso-propyl, sec-butyl, iso-butyl, tert-butyl, phenyl or benzyl, $R^{14}$ and $R^{15}$ are independently from one another selected from the group consisting of $C_1$-$C_6$-alkyl, and $C_6$-aryl-$C_1$-$C_4$-alkyl, wherein the $C_6$-aryl in the $C_6$-$C_{14}$-aryl-$C_1$-$C_4$-alkyl moiety is unsubstituted or substituted by one to five substituents selected from the group consisting of halogen and $C_1$-$C_4$-alkyl, $R^{16}$ and $R^{17}$ are independently from one another phenyl, 1-naphthyl or 2-naphthyl, which in each case is unsubstituted or substituted by one to five substituents selected from the group consisting of halogen, $C_1$-$C_4$-alkyl and $C_1$-$C_4$-haloalkyl, and $R^{18}$ is phenyl, which is unsubstituted or substituted with one to five substituents selected from fluorine and $C_1$-$C_4$-haloalkyl, and in the presence of an additive, wherein the additive is selected from the group consisting of hexafluorophosphoric acid, pentafluorophenol, 3,5-bis(trifluoromethyl)phenol, triphenylborane, tris[3,5-bis(trifluoromethyl)phenyl]borane, tris(2,3,4,5,6-pentafluorophenyl)borane, aluminum (III) trifluoromethanesulfonate, scandium (III) trifluoromethanesulfonate, aluminum (III) fluoride, titanium (IV) isopropoxide, trimethyl aluminum, boron trifluoride, complexes of boron trifluoride, and mixtures thereof, wherein the boron trifluoride complexes are preferably selected from the group consisting of boron trifluoride-diethylether complex, boron trifluoride acetic acid complex and boron trifluoride n-propanol complex.

Particularly preferably the process according to the invention is performed in the presence of a chiral iridium catalyst, wherein the chiral iridium catalyst is selected from the group consisting of chiral iridium catalyst of the formulae (Va), (Vb), (VIa) and (VIb), wherein $R^6$ is selected from the group consisting of phenyl, 2,6- or 3,5-dimethylphenyl, 2,4,6-trimethylphenyl, 4-tert-butylphenyl, 4-methoxyphenyl, 3,5-bis-tert-butyl-4-methoxyphenyl, 4-tert-butyl-2,6-dimethylphenyl, 4-fluorophenyl, 4-trifluoromehtylphenyl, 1-naphtyl, 9-antracenyl, 2,4,6-triisopropylphenyl, 9-phenantryl and 2,6-diethyl-4-methylphenyl, $R^7$ is hydrogen, $R^8$ is hydrogen or methyl $R^9$ and $R^{10}$ are each the same and tert-butyl, adamantly, cyclopentyl or cyclohexyl, m is 1 or 2, $R^{13}$ is tert-butyl, $R^{14}$ and $R^{15}$ are methyl, $R^{16}$ and $R^{17}$ are independently from one another phenyl, which is substituted by one or two methyl, in particular $R^{16}$ and $R^{17}$ are each the same and 2-methylphenyl or 3,5-dimethylphenyl, and $R^{18}$ is 3,5-bis(trifluoromethyl)phenyl, and in the presence of an additive, wherein the additive is selected from the group consisting of aluminum (III) trifluoromethanesulfonate, scandium (III) trifluoromethanesulfonate, tris(2,3,4,5,6-pentafluorophenyl)borane, hexafluorophosphoric acid, boron trifluoride and complexes of boron trifluoride, wherein the boron trifluoride complexes are preferably selected from the group consisting of boron trifluoride-diethylether complex, boron trifluoride acetic acid complex and boron trifluoride n-propanol complex.

The process according to the invention comprises enantioselective hydrogenation of the compound of the formula (II).

Preferably, the hydrogenation is conducted using hydrogen gas at a pressure of from 1 to 300 bar, preferably 3 to 200 bar, most preferably 20 to 150 bar.

The hydrogenation is preferably conducted at a temperature within the range of from 20° C. to 130° C., more preferably 30° C. to 100° C.

Suitable solvents are halogenated alcohols such as 2,2,2-trifluoroethanol, hexafluoroisopropanol (1,1,1,3,3,3-hexafluoro-2-propanol) and tetrafluoropropanol (2,2,3,3-tetrafluoro-1-propanol), halogenated hydrocarbons, such as chlorobenzene, dichlorobenzene, dichloromethane, chloroform, tetrachloromethane, dichloroethane and trichloroethane, aromatic hydrocarbons such as benzene, toluene and xylene, ethers such as diethyl ether, diisopropyl ether, methyl tert-butyl ether, methyl tert-amyl ether, dioxane, tetrahydrofuran, 1,2-dimethoxyethane, 1,2-diethoxyethane and anisole, and esters such as ethyl acetate, isopropyl acetate, and mixtures thereof.

Preferred solvents are selected from the group consisting of 2,2,2-trifluoroethanol, hexafluoroisopropanol, 1,2-dichloroethane, tetrafluoropropanol, 1,4-dioxane, isopropyl acetate, toluene, and mixtures thereof.

More preferred solvents are selected from the group consisting of 2,2,2-trifluoroethanol, hexafluoroisopropanol, 1,2-dichloroethane, tetrafluoropropanol, and mixtures thereof.

Especially preferred are 2,2,2-trifluoroethanol and hexafluoroisopropanol.

Most preferred is hexafluoroisopropanol.

Abbreviations and Acronyms

| a/a | |
|---|---|
| Ac | Acetyl |
| c-hexane | cyclohexane |
| Cy | Cyclohexyl |
| DCM | dichloromethane |
| GC-FID | Gas chromatography-Flame ionization detector |
| HPLC | High performance liquid chromatography |
| Et | Ethyl |
| Me | Methyl |
| n-BuLi | n-Butyllithium |
| PTFE | Polytetrafluoroethylene |
| RT | Room temperature |
| SFC | Supercritical fluid chromatography |
| THF | tetrahydrofurane |
| Tf | Trifluoromethylsulfonyl |
| TFE | 2,2,2-Trifluoroethanol |

Preparation of Iridium Catalysts

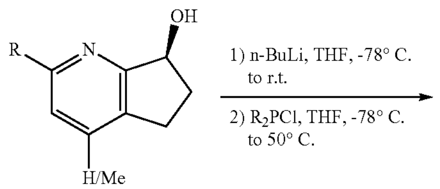

-continued

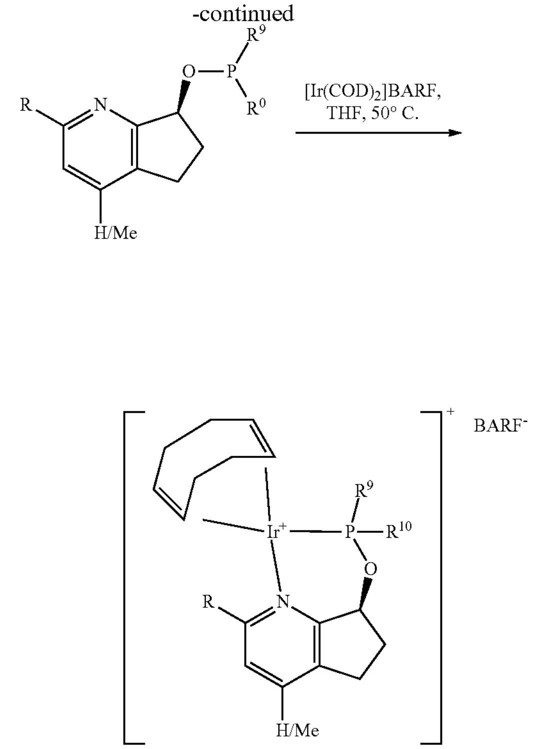

The ligand precursors (enantiomerically enriched secondary alcohols) were prepared according to known literature procedures like to the method disclosed in S. Kaiser et al., Angew. Chem. Int. Ed. 2006, 45, 5194-5197 or in D. H. Woodmansee Chem. Sci 2010, 1, 72. The ligands and iridium complexes were prepared by a modified procedure based on the same literature precedents:

Standard Procedures

Procedure of ligand synthesis (under Ar): A solution of alcohol precursor in THF (0.25 mmol, in 5.0 mL THF) was cooled to −78° C. and n-BuLi (0.1 mL of a 2.5 M n-BuLi solution in hexane; 0.25 mmol; 1 eq.) was added dropwise to the continuously stirred solution. After completion of the addition the solution was allowed to warm to room temperature and was stirred at this temperature for further 30 min. The solution was cooled to −78° C. again and $R_2PCl$ (0.25 mmol, 1 eq.) was added to the continuously stirred solution. The mixture was allowed to warm to room temperature and subsequently heated to 50° C. and kept at this temperature overnight. The theoretical yield of ligand was calculated using $^{31}P$-NMR and the ligand was used for the next step without further purification.

Procedure of complexation (under Ar): To the crude ligand solution was added $[Ir(COD)_2]BARF$ (BARF=Tetrakis[3,5-bis(trifluoromethyl)phenyl]-borate) (as a solid, 1 eq. based on the theoretical yield). The resulting mixture was heated to 50° C. and kept at this temperature for 3 h.

Work-up (under air): After cooling to room temperature the reaction solution is rotary evaporated onto silica, loaded onto a column of silica. Side components were eluted using pentane/diethylether and the desired complexes subsequently with DCM. The solvent was then evaporated under reduced pressure.

The following catalysts were synthesized and characterized:

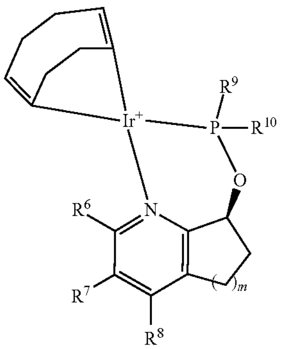

$[B(R^{18})_4]^-$ with m=1 and $R^{18}$=3,5-bis(trifluoromethyl)phenyl

TABLE 1

| Catalyst | $R^6$ | $R^7$ | $R^8$ | $R^9$, $R^{10}$ |
|---|---|---|---|---|
| Va-1 | phenyl | H | H | tert-butyl |
| Va-2 | phenyl | H | methyl | tert-butyl |
| Vb-3 | phenyl | H | H | cyclohexyl |
| Va-4 | phenyl | H | methyl | cyclohexyl |
| Vb-5 | 4-tert-butylphenyl | H | H | cyclohexyl |
| Va-6 | 4-tert-butylphenyl | H | methyl | cyclohexyl |
| Vb-7 | 9-antracenyl | H | H | cyclohexyl |
| Va-8 | 9-antracenyl | H | methyl | cyclohexyl |
| Va-9 | 2,6-dimethylphenyl | H | methyl | cyclohexyl |
| Va-10 | 2,4,6-trimethylphenyl | H | methyl | cyclohexyl |
| Va-11 | 3,5-dimethylphenyl | H | methyl | cyclohexyl |
| Va-12 | 1-naphtyl | H | methyl | cyclohexyl |
| Va-13 | 4-methoxyphenyl | H | methyl | tert-butyl |
| Va-14 | 4-fluorophenyl | H | methyl | tert-butyl |
| Va-15 | 4-(trifluoromethyl)phenyl | H | methyl | tert-butyl |
| Va-16 | phenyl | H | methyl | cyclopentyl |
| Vb-17 | phenyl | H | H | ethyl |
| Va-18 | phenyl | H | methyl | isopropyl |
| Va-19 | methyl | H | methyl | cyclohexyl |
| Va-20 | 3,5-bis-tert.-butyl,-4-methoxyphenyl | H | methyl | cyclohexyl |
| Va-21 | 2,4,6-triisopropylphenyl | H | methyl | cyclohexyl |
| Va-22 | 4-tert-butyl-2,6-dimethylphenyl | H | methyl | cyclohexyl |
| Va-23 | phenyl | H | H | adamantyl |
| Va-24 | 9-phenantryl | H | methyl | cyclohexyl |
| Va-25 | 2,6-diethyl-4-methylphenyl | H | methyl | cyclohexyl |
| Va-26* | 4-tert-butyl-2,6-dimethylphenyl | H | methyl | cyclohexyl |

*Counteranion is $PF_6$ instead of BARF

Va-2

The reaction was performed according to the above described standard procedure. The complex could be isolated as an orange solid (89.5 mg; 53% based on $[Ir(COD)_2]$BARF).

$^1$H-NMR (300 MHz, $CD_2Cl_2$): δ (ppm)=8.26 (dd, J=7.9, 1.7 Hz, 2H), 7.81-7.36 (m, 16H), 5.75 (dt, J=8.0, 5.2 Hz, 1H), 5.34-5.29 (m, 1H), 4.51 (q, J=5.3, 3.2 Hz, 1H), 4.11 (dq, J=12.5, 7.6, 5.9 Hz, 1H), 3.08 (ddd, J=16.6, 10.3, 3.8 Hz, 1H), 2.99-2.70 (m, 2H), 2.61-2.00 (m, 8H), 1.92-1.79 (m, 1H), 1.69 (dd, J=14.8, 8.1 Hz, 1H), 1.51 (s, 9H), 1.29-1.24 (m, 3H), 1.06 (d, J=14.4 Hz, 9H). $^{31}$P-NMR (122 MHz, $CD_2Cl_2$) δ (ppm)=142.09. $^{19}$F-NMR (282 MHz, $CD_2Cl_2$) δ (ppm)=−62.85. HR-MS (ESI) m/z calcd for $C_{31}H_{44}$NOPIr [M]+ 670.2790 found 670.2798.

Va-4

The reaction was performed according to the above described standard procedure. The complex could be isolated as an orange solid (241 mg; 71% based on $[Ir(COD)_2]$BARF).

$^1$H-NMR (300 MHz, $CD_2Cl_2$): δ (ppm)=8.38-8.14 (m, 2H), 7.83-7.43 (m, 16H), 5.76 (dt, J=7.7, 4.9 Hz, 1H), 4.81 (t, J=7.6 Hz, 1H), 4.70-4.46 (m, 1H), 3.56-3.39 (m, 1H), 3.06 (ddd, J=16.7, 10.3, 3.6 Hz, 1H), 2.98-2.73 (m, 2H), 2.71-2.57 (m, 1H), 2.44 (s, 3H), 2.41-2.02 (m, 6H), 2.00-1.75 (m, 7H), 1.72-1.54 (m, 4H), 1.46-0.94 (m, 13H), 0.72-0.50 (m, 1H). $^{31}$P-NMR (122 MHz, $CD_2Cl_2$) δ (ppm)=121.27. $^{19}$F-NMR (282 MHz, $CD_2Cl_2$) δ (ppm)=−62.86. HR-MS (ESI) m/z calcd for $C_{35}H_{48}$NOPIr [M]+ 722.3103 found 722.3116.

Vb-5

The reaction was performed according to the above described standard procedure using 287 mg of $[Ir(COD)_2]$BARF (0.225 mmol). The complex could be isolated as an orange solid (261 mg; 74% based on $[Ir(COD)_2]$BARF).

$^1$H-NMR (300 MHz, $CD_2Cl_2$): δ (ppm)=8.25 (d, J=8.3 Hz, 2H), 7.87 (d, J=8.1 Hz, 1H), 7.81-7.64 (m, 11H), 7.56 (s, 4H), 5.74 (dt, J=8.2, 4.6 Hz, 1H), 4.95-4.74 (m, 1H), 4.74-4.51 (m, 1H), 3.60-3.45 (m, 1H), 3.23-2.91 (m, 2H), 2.90-2.70 (m, 1H), 2.67-2.50 (m, 1H), 2.52-2.23 (m, 4H), 2.28-2.04 (m, 3H), 2.04-1.77 (m, 7H), 1.69-1.58 (m, 4H), 1.45-1.26 (m, 17H), 1.17-0.95 (m, 4H), 0.68-0.42 (m, 1H). $^{31}$P-NMR (122 MHz, $CD_2Cl_2$) δ (ppm)=121.12. $^{19}$F-NMR (282 MHz, $CD_2Cl_2$) δ (ppm)=−62.85. HR-MS (ESI) m/z calcd for $C_{38}H_{54}$NOPIr [M]+ 764.3572 found 764.3586.

Va-6

The reaction was performed according to the above described standard procedure. The complex could be isolated as an orange solid (286 mg; 64% based on $[Ir(COD)_2]$BARF).

$^1$H-NMR (300 MHz, $CDCl_3$): δ (ppm)=8.20 (d, J=8.2 Hz, 2H), 7.77-7.69 (m, 8H), 7.66 (d, J=8.4 Hz, 2H), 7.53 (d, J=4.9 Hz, 5H), 5.77-5.67 (m, 1H), 4.78 (d, J=7.6 Hz, 1H), 4.57 (s, 1H), 3.47 (s, 1H), 3.08-2.89 (m, 1H), 2.89-2.66 (m, 2H), 2.59 (p, J=7.4 Hz, 1H), 2.47-1.74 (m, 15H), 1.42 (s, 17H), 1.18-0.78 (m, 5H), 0.72-0.48 (m, 1H). $^{31}$P-NMR (122 MHz, $CDCl_3$) 121.31. $^{19}$F-NMR (282 MHz, $CDCl_3$) δ=−62.42. HR-MS (ESI): m/z calculated for $[C_{39}H_{56}$NOP193 Ir]+: 778.3729 found 778.3732.

Vb-7

The reaction was performed according to the above described standard procedure using 287 mg of $[Ir(COD)_2]$BARF (0.225 mmol). The complex could be isolated after two time purification as an orange solid (151 mg; 36% based on $[Ir(COD)_2]$BARF).

$^1$H-NMR (300 MHz, $CD_2Cl_2$): δ (ppm)=8.84 (s, 1H), 8.38-8.27 (m, 1H), 8.21 (ddt, J=8.5, 1.3, 0.7 Hz, 1H), 8.18-8.02 (m, 2H), 7.83-7.72 (m, 10H), 7.72-7.54 (m, 6H), 7.49 (ddd, J=8.8, 6.6, 1.4 Hz, 1H), 7.23-6.96 (m, 1H), 5.74-5.54 (m, 1H), 5.26-5.12 (m, 1H), 4.41-4.18 (m, 1H), 3.53-3.15 (m, 3H), 2.75-2.61 (m, 2H), 2.59-2.32 (m, 2H), 2.18-1.91 (m, 6H), 1.92-1.74 (m, 5H), 1.74-1.56 (m, 2H), 1.48-1.21 (m, 10H), 1.18-0.99 (m, 1H), 0.96-0.59 (m, 2H), 0.39-0.15 (m, 1H), 0.06-−0.11 (m, 1H). $^{31}$P-NMR (122 MHz, $CD_2Cl_2$) δ (ppm)=120.30. $^{19}$F-NMR (282 MHz, $CD_2Cl_2$) δ (ppm)=−62.87. HR-MS (ESI) m/z calcd for $C_{42}H_{50}$NOPIr [M]+ 808.3259 found 808.3278.

Va-8

The reaction was performed according to the above described standard procedure using 287 mg of $[Ir(COD)_2]$BARF (0.225 mmol). The complex could be isolated using DCM (100%) to afford an orange solid (296 mg; 78% based on $[Ir(COD)_2]$BARF).

$^{1}$H-NMR (300 MHz, $CD_2Cl_2$): δ (ppm)=8.68 (s, 1H), 8.23-7.85 (m, 3H), 7.75-7.23 (m, 17H), 7.05 (dq, J=8.8, 1.0 Hz, 1H), 5.61-5.40 (m, 2H), 5.12-4.88 (m, 1H), 4.24-4.00 (m, 1H), 3.25-2.88 (m, 3H), 2.58-2.46 (m, 2H), 2.44-2.14 (m, 7H), 2.08-1.61 (m, 11H), 1.61-1.37 (m, 5H), 1.37-1.07 (m, 6H), 1.03-0.85 (m, 1H), 0.65-0.45 (m, 1H), 0.16 (dtd, J=15.8, 10.4, 5.6 Hz, 1H), −0.16 (dt, J=13.2, 9.1 Hz, 1H). $^{31}$P-NMR (122 MHz, CD2Cl2) δ=120.57. $^{19}$F-NMR (282 MHz, CD2Cl2) δ=−62.86. HR-MS (ESI) m/z calcd for $C_{43}H_{52}NOPIr$ [M]+ 822.3416 found 822.3416.

Va-9

The reaction was performed according to the above described standard procedure using 287 mg of $[Ir(COD)_2]$ BARF (0.225 mmol). The complex could be isolated as an orange solid (298 mg; 82% based on $[Ir(COD)_2]$BARF).

$^{1}$H-NMR (300 MHz, $CD_2Cl_2$): δ (ppm)=7.80-7.52 (m, 12H), 7.42-7.19 (m, 3H), 7.12 (d, J=7.5 Hz, 1H), 5.65 (td, J=5.6, 2.6 Hz, 1H), 5.48-5.42 (m, 1H), 4.43-4.37 (m, 1H), 3.38-3.30 (m, 1H), 3.21-2.89 (m, 3H), 2.67 (s, 3H), 2.58-2.45 (m, 2H), 2.42 (s, 3H), 2.38-2.16 (m, 2H), 2.13-2.05 (m, 3H), 2.02-1.89 (m, 4H), 1.84 (s, 3H), 1.81-1.72 (m, 2H), 1.64-1.49 (m, 3H), 1.39-1.19 (m, 8H), 1.12-0.99 (m, 4H), 0.68-0.56 (m, 1H). $^{31}$P-NMR (122 MHz, $CD_2Cl_2$) 6=118.80. $^{19}$F-NMR (282 MHz, $CD_2Cl_2$) 6=−62.88. HR-MS (ESI) m/z calcd for $C_{37}H_{52}NOPIr$ [M]+ 750.3416 found 750.3420.

Va-10

The reaction was performed according to the above described standard procedure using 287 mg of $[Ir(COD)_2]$ BARF (0.225 mmol). The complex could be isolated as an orange solid (148 mg; 40% based on $[Ir(COD)_2]$BARF).

$^{1}$H-NMR (300 MHz, $CD_2Cl_2$): δ (ppm)=7.91-7.46 (m, 12H), 7.21 (s, 1H), 7.09 (s, 1H), 6.94 (s, 1H), 5.67-5.63 (m, 1H), 5.46-5.41 (m, 1H), 4.38-4.36 (m, 1H), 3.36-3.32 (m, 1H), 3.19-2.85 (m, 3H), 2.64 (s, 3H), 2.53-2.46 (m, 2H), 2.41 (s, 3H), 2.35 (s, 3H), 2.31-2.18 (m, 2H), 2.19-1.83 (m, 14H), 1.68-1.54 (m, 6H), 1.38-1.20 (m, 5H), 1.14-0.97 (m, 5H), 0.68-0.56 (m, 1H). $^{31}$P-NMR (122 MHz, $CD_2Cl_2$) δ=118.64. $^{19}$F-NMR (282 MHz, $CD_2Cl_2$) δ=−62.87. HR-MS (ESI) m/z calcd for $C_{38}H_{54}NOPIr$ [M]+ 764.3572 found 764.3577.

Va-11

The reaction was performed according to the above described standard procedure using 287 mg of $[Ir(COD)_2]$ BARF (0.225 mmol). The complex could be isolated using DCM (100%) to afford an orange solid (310 mg; 85% based on $[Ir(COD)_2]$BARF).

$^{1}$H-NMR (300 MHz, $CD_2Cl_2$): δ (ppm)=7.86 (s, 2H), 7.79-7.47 (m, 13H), 7.36 (s, 1H), 5.79-5.62 (m, 1H), 4.78-4.74 (m, 1H), 4.57-4.53 (m, 1H), 3.56-3.48 (m, 1H), 3.13-2.95 (m, 1H), 2.95-2.61 (m, 3H), 2.51 (s, 6H), 2.47-2.36 (m, 5H), 2.34-2.03 (m, 5H), 2.03-1.77 (m, 7H), 1.71-1.47 (m, 7H), 1.45-1.19 (m, 5H), 1.19-0.98 (m, 4H), 0.70-0.62 (m, 1H). $^{31}$P-NMR (122 MHz, $CD_2Cl_2$) δ=121.65. $^{19}$F-NMR (282 MHz, $CD_2Cl_2$) δ=−62.88. HR-MS (ESI) m/z calcd for $C_{37}H_{52}NOPIr$ [M]+ 750.3416 found 750.3406.

Va-12

The reaction was performed according to the above described standard procedure using 287 mg of $[Ir(COD)_2]$ BARF (0.225 mmol). The complex could be isolated as an orange solid (286 mg; 78% based on $[Ir(COD)_2]$BARF).

$^{1}$H-NMR (300 MHz, $CD_2Cl_2$): δ (ppm)=8.61-8.48 (m, 1H), 8.28-8.15 (m, 1H), 8.11-7.98 (m, 1H), 7.98-7.81 (m, 1H), 7.79-7.50 (m, 16H), 5.70 (ddd, J=8.1, 4.9, 3.2 Hz, 1H), 5.37-5.25 (m, 1H), 4.79 (d, J=10.4 Hz, 1H), 3.53-3.41 (m, 1H), 3.13 (ddd, J=17.2, 9.5, 4.9 Hz, 1H), 2.96 (ddd, J=17.1, 9.4, 4.9 Hz, 1H), 2.88-2.66 (m, 1H), 2.49-2.34 (m, 7H), 2.27-2.14 (m, 1H), 2.09-1.56 (m, 15H), 1.43-1.12 (m, 9H), 1.06-0.92 (m, 1H), 0.78-0.59 (m, 1H), 0.42-0.25 (m, 1H). $^{31}$P-NMR (122 MHz, $CD_2Cl_2$) δ=121.69. $^{19}$F-NMR (282 MHz, $CD_2Cl_2$) δ=−62.87. HR-MS (ESI) m/z calcd for $C_{39}H_{50}NOPIr$ [M]+ 722.3259 found 722.3262.

Va-13

The reaction was performed according to the above described standard procedure. The theoretical yield of the ligand was 51%. The complex could be isolated as an orange solid (78.0 mg; 39% based on $[Ir(COD)_2]$BARF).

$^{1}$H-NMR (300 MHz, $CDCl_3$): δ (ppm)=8.22 (d, J=8.7 Hz, 2H), 7.80-7.63 (m, 8H), 7.63-7.43 (m, 5H), 7.16 (d, J=8.8 Hz, 2H), 5.82-5.66 (m, 1H), 5.37-5.22 (m, 1H), 4.56-4.41 (m, 1H), 4.18-4.00 (m, 1H), 3.93 (s, 3H), 3.12-2.97 (m, 1H), 2.96-2.74 (m, 2H), 2.70-2.56 (m, 1H), 2.43 (s, 3H), 2.41-2.03 (m, 4H), 1.96-1.84 (m, 1H), 1.72 (dd, J=14.6, 7.9 Hz, 1H), 1.51 (d, J=15.0 Hz, 9H), 1.34-1.23 (m, 3H), 1.05 (d, J=14.4 Hz, 9H). $^{31}$P-NMR (122 MHz, $CD_2Cl_2$) δ (ppm) =141.86. $^{19}$F-NMR (282 MHz, $CD_2Cl_2$) δ (ppm)=−62.85. HR-MS (ESI) m/z calcd for $C_{32}H_{46}NO_2PIr$ [M]+ 700.2895 found 700.2899.

Va-14

The reaction was performed according to the above described standard procedure using 287 mg of $[Ir(COD)^2]$ BARF (0.225 mmol). The complex could be isolated as an orange solid (245 mg; 70% based on $[Ir(COD)^2]$BARF).

$^{1}$H-NMR (300 MHz, $CDCl_3$): δ (ppm)=8.38-8.12 (m, 2H), 7.82-7.63 (m, 8H), 7.51 (s, 5H), 7.44-7.17 (m, 2H), 5.81-5.63 (m, 1H), 4.81-4.67 (m, 1H), 4.67-4.49 (m, 1H), 3.57-3.35 (m, 1H), 3.05-2.90 (m, 1H), 2.88-2.61 (m, 3H), 2.36 (s, 3H), 2.31-2.04 (m, 7H), 2.01-1.73 (m, 7H), 1.70-1.48 (m, 6H), 1.42-1.20 (m, 6H), 1.16-0.97 (m, 4H), 0.63-0.40 (m, 1H). $^{31}$P-NMR (122 MHz, $CDCl_3$) δ (ppm) =121.31. $^{19}$F-NMR (282 MHz, $CDCl_3$) δ (ppm)=−62.43, −106.61. HR-MS (ESI) m/z calcd for $C_{35}H_{47}NOFPIr$ [M]+ 740.3009 found 740.3013.

Va-15

The reaction was performed according to the above described standard procedure using 287 mg of $[Ir(COD)_2]$ BARF (0.225 mmol). The complex could be isolated as an orange solid (180.0 mg; 48% based on $[Ir(COD)_2]$BARF).

$^{1}$H-NMR (300 MHz, $CD_2Cl_2$): δ (ppm)=8.46 (d, J=7.9 Hz, 2H), 7.94 (d, J=8.0 Hz, 2H), 7.82-7.38 (m, 13H), 5.83-5.69 (m, 1H), 4.94-4.78 (m, 1H), 4.73-4.54 (m, 1H), 3.65-3.38 (m, 1H), 3.15-2.72 (m, 3H), 2.61-2.27 (m, 7H), 2.25-2.04 (m, 4H), 2.04-1.72 (m, 8H), 1.75-1.58 (m, 3H), 1.43-1.22 (m, 8H), 1.19-0.93 (m, 1H), 0.63-0.44 (m, 1H). $^{31}$P-NMR (122 MHz, $CD_2Cl_2$) δ (ppm)=121.74. $^{19}$F-NMR (282 MHz, $CD_2Cl_2$) δ (ppm)=−62.88, −63.40. HR-MS (ESI) m/z calcd for $C_{36}H_{47}NOF_3PIr$ [M]+ 790.2977 found 790.2990.

Va-16

The reaction was performed according to the above described standard procedure. The theoretical yield of the ligand was 90%. The complex could be isolated as an orange solid (261 mg; 75% based on $[Ir(COD)_2]$BARF).

$^{1}$H-NMR (300 MHz, $CD_2Cl_2$): δ (ppm)=8.28-8.11 (m, 2H), 7.93-7.45 (m, 16H), 5.81 (dt, J=9.3, 5.0 Hz, 1H), 4.89 (t, J=6.9 Hz, 1H), 4.72-4.51 (m, 1H), 3.86-3.66 (m, 1H), 3.18-3.04 (m, 1H), 3.04-2.57 (m, 4H), 2.49 (s, 3H), 2.46-1.61 (m, 18H), 1.56-1.36 (m, 5H), 1.36-1.14 (m, 1H), 1.13-0.93 (m, 1H), 0.77-0.66 (m, 1H). $^{31}$P-NMR (122 MHz, $CD_2Cl_2$) δ (ppm)=129.37. $^{19}$F-NMR (282 MHz, $CD_2Cl_2$) δ (ppm)=−62.88. HR-MS (ESI) m/z calcd for $C_{33}H_{44}NOPIr$ [M]+ 694.2790 found 694.2789.

Vb-17

The reaction was performed according to the above described standard procedure. The complex could be isolated as an orange solid (134 mg; 95% purity based on 31P-NMR; 39% based on $[Ir(COD)_2]BARF$).

$^1$H-NMR (300 MHz, $CDCl_3$): δ (ppm)=8.00-7.92 (m, 2H), 7.81-7.76 (m, 1H), 7.75-7.64 (m, 10H), 7.62-7.55 (m, 2H), 7.52 (d, J=1.9 Hz, 4H), 5.88 (dt, J=8.3, 4.9 Hz, 1H), 4.52 (dt, J=8.3, 4.2 Hz, 1H), 4.37 (ddt, J=7.4, 5.0, 2.5 Hz, 1H), 3.61 (td, J=8.0, 3.8 Hz, 1H), 3.17-2.64 (m, 4H), 2.34-1.79 (m, 9H), 1.68-1.55 (m, 1H), 1.36-0.90 (m, 9H). $^{31}$P-NMR (122 MHz, $CDCl_3$) δ=116.36 (mayor product; 95%), 111.79 (minor species; 5%). $^{19}$F-NMR (282 MHz, $CDCl_3$) δ=−62.41. HR-MS (ESI) m/z calcd for $C_{26}H_{34}NOPIr$ [M]+ 600.2006 found 600.2006.

Va-18

The reaction was performed (0.5 mmol scale) according to the above described standard procedure, but after the addition of $ClP(iPr)_2$ was completed, the reaction mixture was stirred at RT for 16 h. The complex could be isolated as an orange solid (605 mg; 85% based on $[Ir(COD)_2]BARF$).

$^1$H-NMR (300 MHz, $CDCl_3$): δ (ppm)=8.17 (dd, J=7.1, 1.8 Hz, 2H), 7.78-7.40 (m, 16H), 5.74 (dt, J=9.0, 4.7 Hz, 1H), 4.83 (t, J=6.9 Hz, 1H), 4.61 (dt, J=8.7, 4.1 Hz, 1H), 3.62-3.53 (m, 1H), 3.11-2.94 (m, 1H), 2.91-2.67 (m, 2H), 2.67-2.44 (m, 2H), 2.39 (s, 3H), 2.36-1.93 (m, 6H), 1.85 (dd, J=14.5, 7.3 Hz, 1H), 1.46 (dd, J=15.2, 7.1 Hz, 3H), 1.39-1.31 (m, 1H), 1.23 (dd, J=13.3, 6.9 Hz, 4H), 1.08 (dd, J=19.4, 7.1 Hz, 3H), 0.52 (dd, J=15.5, 7.1 Hz, 3H). $^{31}$P-NMR (122 MHz, $CDCl_3$) δ (ppm)=129.53. $^{19}$F-NMR (282 MHz, $CDCl_3$) δ (ppm)=−62.42. HR-MS (ESI) m/z calcd for $C_{29}H_{40}NOPIr$ [M]+ 642.2477 found 642.2480.

Va-19

The reaction was performed according to the above described standard procedure. The complex could be isolated as an orange solid (249 mg; 73% based on $[Ir(COD)_2]BARF$).

$^1$H-NMR (300 MHz, $CD_2Cl_2$): δ (ppm)=7.81-7.61 (m, 9H), 7.56 (d, J=2.0 Hz, 4H), 7.34 (d, J=8.0 Hz, 1H), 5.76 (dt, J=8.7, 4.5 Hz, 1H), 5.05-4.84 (m, 2H), 3.74-3.57 (m, 1H), 3.56-3.36 (m, 1H), 3.07 (s, 3H), 3.01-1.49 (m, 23H), 1.42-1.01 (m, 9H), 0.85-0.70 (m, 1H), 0.51-0.25 (m, 1H). $^{31}$P-NMR (122 MHz, $CD_2Cl_2$) δ (ppm)=126.20. $^{19}$F-NMR (282 MHz, $CD_2Cl_2$) δ (ppm)=−62.88. HR-MS (ESI) m/z calcd for $C_{29}H_{44}NOPIr$ [M]+ 644.2766 found 644.2762.

Va-20

The reaction was performed according to the above described standard procedure. The complex could be isolated as an orange solid (164 mg; 42% based on $[Ir(COD)_2]BARF$).

$^1$H-NMR (300 MHz, $CD_2Cl_2$): δ (ppm)=7.86-7.62 (m, 10H), 7.56 (s, 4H), 7.38 (s, 1H), 5.72 (dt, J=8.1, 5.2 Hz, 1H), 4.85-4.63 (m, 2H), 3.80 (s, 3H), 3.49-3.30 (m, 1H), 3.18-2.60 (m, 4H), 2.54-2.23 (m, 6H), 2.23-1.57 (m, 16H), 1.53-1.49 (m, 20H), 1.46-0.93 (m, 10H). $^{31}$P-NMR (122 MHz, $CD_2Cl_2$) δ (ppm)=123.26. $^{19}$F-NMR (282 MHz, $CD_2Cl_2$) δ (ppm)=−62.87. HR-MS (ESI) m/z calcd for $C_{44}H_{66}NO_2PIr$ [M]+ 864.4460 found 864.4448.

Va-21

The reaction was performed according to the above described standard procedure. The complex could be isolated as an orange solid (51 mg; 14% based on $[Ir(COD)_2]BARF$).

$^1$H-NMR (400 MHz, $CD_2Cl_2$): δ (ppm)=7.80-7.64 (m, 8H), 7.56 (s, 4H), 7.23 (s, 2H), 7.04 (s, 1H), 5.65 (dt, J=5.9, 3.7 Hz, 1H), 5.45-5.35 (m, 1H), 4.04 (ddd, J=8.2, 5.4, 3.6 Hz, 1H), 3.34 (dd, J=11.2, 6.4 Hz, 1H), 3.19-3.08 (m, 3H), 3.06-2.89 (m, 2H), 2.56-2.44 (m, 2H), 2.41 (s, 3H), 2.33-1.84 (m, 9H), 1.84-1.43 (m, 15H), 1.35-1.24 (m, 12H), 1.23-1.14 (m, 5H), 1.09 (dd, J=10.0, 6.8 Hz, 6H), 0.95 (d, J=6.6 Hz, 3H), 0.60-0.46 (m, 1H). $^{31}$P-NMR (162 MHz, $CD_2Cl_2$) δ (ppm)=119.43. $^{19}$F-NMR (282 MHz, $CD_2Cl_2$) δ (ppm)=−62.86. HR-MS (ESI) m/z calcd for $C_{44}H_{66}NOPIr$ [M]+ 848.4511 found 848.4512.

Va-22

The reaction was performed according to the above described standard procedure. The complex could be isolated as an orange solid (274 mg; 73% based on $[Ir(COD)_2]BARF$).

$^1$H-NMR (300 MHz, $CD_2Cl_2$): δ (ppm)=7.79-7.66 (m, 8H), 7.56 (s, 4H), 7.29 (s, 1H), 7.23 (s, 1H), 7.13 (s, 1H), 5.65 (td, J=5.9, 2.2 Hz, 1H), 5.46-5.40 (m, 1H), 4.42-4.36 (m, 1H), 3.38-3.30 (m, 1H), 3.19-2.86 (m, 3H), 2.65 (s, 3H), 2.59-2.44 (m, 2H), 2.42 (s, 3H), 2.38-1.54 (m, 20H), 1.46-0.98 (m, 21H), 0.70-0.58 (m, 1H). $^{31}$P-NMR (122 MHz, $CD_2Cl_2$) δ (ppm)=118.67. $^{19}$F-NMR (282 MHz, $CD_2Cl_2$) δ (ppm)=−62.86. HR-MS (ESI) m/z calcd for $C_{41}H_{60}NOPIr$ [M]+ 806.4042 found 806.4053.

Va-23

The reaction was performed according to the above described standard procedure. The complex could be isolated as an orange solid (15.6 mg; 20% based on $[Ir(COD)_2]BARF$).

$^1$H-NMR (300 MHz, $CD_2Cl_2$) δ=8.43-8.36 (m, 2H), 7.92-7.85 (m, 1H), 7.81-7.69 (m, 12H), 7.68-7.53 (m, 4H), 5.73-5.65 (m, 1H), 5.50-5.43 (m, 1H), 4.58-4.43 (m, 2H), 3.25-3.12 (m, 1H), 3.08-2.94 (m, 1H), 2.92-2.77 (m, 1H), 2.72-1.45 (m, 40H). $^{19}$F-NMR (282 MHz, $CDCl_3$) δ=−62.42. $^{31}$P-NMR (122 MHz, $CD_2Cl_2$) δ=134.32. HR-MS (TOF) m/z calcd for $C_{42}H_{54}NOPIr$ [M]+ 812.3572 found 812.3578.

Va-24

The reaction was performed according to the above described standard procedure. The complex could be isolated as an orange solid (274 mg; 72% based on $[Ir(COD)_2]BARF$).

$^1$H-NMR (300 MHz, $CD_2Cl_2$) δ=8.99-8.77 (m, 3H), 8.04-7.63 (m, 15H), 7.56 (s, 4H), 5.72-5.63 (m, 1H), 4.88-4.83 (m, 1H), 4.74-4.68 (m, 1H), 3.49-3.40 (m, 1H), 3.27-3.07 (m, 1H), 3.08-2.91 (m, 1H), 2.86-2.74 (m, 1H), 2.61-2.36 (m, 6H), 2.19 (ddd, J=15.6, 13.8, 8.1 Hz, 1H), 2.11-1.11 (m, 25H), 0.99-0.66 (m, 3H). $^{31}$P-NMR (122 MHz, $CD_2Cl_2$) δ=121.93. $^{19}$F-NMR (282 MHz, $CD_2Cl_2$) δ=−62.86. HR-MS (ESI) m/z calcd for $C_{43}H_{52}NOPIr$ $[M]^+$ 822.3410 found 822.3436.

Va-25

The reaction was performed according to the above described standard procedure. The complex could be isolated as an orange solid (282 mg; 76% based on $[Ir(COD)_2]BARF$).

$^1$H-NMR (300 MHz, $CD_2Cl_2$): δ (ppm)=7.73 (s, 8H), 7.56 (s, 4H), 7.23 (s, 1H), 7.14 (s, 1H), 7.00 (s, 1H), 5.62 (dd, J=8.0, 5.6 Hz, 1H), 5.46-5.39 (m, 1H), 4.32 (dd, J=7.4, 3.4 Hz, 1H), 3.36-3.27 (m, 1H), 3.19-3.06 (m, 2H), 3.01-2.91 (m, 2H), 2.80 (dq, J=14.9, 7.4 Hz, 1H), 2.59-2.43 (m, 2H), 2.43-2.15 (m, 7H), 2.15-0.83 (m, 36H), 0.66-0.48 (m, 1H). $^{31}$P-NMR (122 MHz, $CD_2Cl_2$) δ (ppm)=119.00. $^{19}$F-NMR (282 MHz, $CD_2Cl_2$) δ (ppm)=−62.87. HR-MS (ESI) m/z calcd for $C_{40}H_{58}NOPIr$ [M]+ 792.3880 found 792.3903.

Va-26

A solution of the respective alcohol precursor in THF (0.25 mmol, in 5.0 mL THF) was cooled to −78° C. and n-BuLi (0.1 mL of a 2.5 M n-BuLi solution in hexane; 0.25 mmol; 1 eq.) was added dropwise to the continuously stirred solution. After completion of the addition the solution was allowed to warm to room temperature and was stirred at this temperature for further 30 min. The solution was cooled to −78° C. again and $Cy_2PCl$ (0.25 mmol, 1 eq.) was added to the continuously stirred solution. The mixture was allowed to warm to room temperature and subsequently heated to 50° C. and kept at this temperature overnight. After the reaction was cooled down to RT, THF was removed and dried in vacuum, $[Ir(cod)Cl]_2$ (0.125 mmol) and DCM (5.0 mL) were added to the tube, stirred at 50° C. for 2 h. Then $KPF_6$ (0.25 mmol) was added to the reaction mixture and stirred at RT for overnight. The reaction solution is rotary evaporated onto silica, loaded onto a column of silica prepared with DCM chromatographed with EtOAc/DCM: 1/10 to afford the orange solid after two times column chromatography (130 mg, 55%).

$^1$H-NMR (300 MHz, $CD_2Cl_2$) δ=7.37-7.02 (m, 3H), 5.74-5.56 (m, 1H), 5.52-5.46 (m, 1H), 4.47-4.30 (m, 1H), 3.45-3.21 (m, 1H), 3.19-2.92 (m, 3H), 2.66 (s, 3H), 2.63-2.48 (m, 2H), 2.44 (s, 3H), 2.40-2.19 (m, 2H), 2.16-1.70 (m, 15H), 1.68-1.46 (m, 6H), 1.41-1.28 (m, 13H), 1.18-0.95 (m, 5H), 0.71-0.58 (m, 1H). $^{31}$P-NMR (122 MHz, $CD_2Cl_2$) δ=118.42, −127.01, −132.85, −138.70, −144.55, −150.39, −156.24, −162.09. $^{19}$F-NMR (376 MHz, $CD_2Cl_2$) δ=−72.64, −74.52. HR-MS (ESI) m/z calcd for $C_{41}H_{60}NOPIr$ $[M]^+$ 806.4036 found 806.4061.

EXAMPLES

Reactions were performed in metal autoclaves. Reaction mixtures were analyzed without workup via HPLC (Chiralpak IC column, 95/5 heptane/ethanol, 1 mL/min) or SFC (OZ-H column, 2.5% MeOH in supercritical $CO_2$, 3 mL/min) chromatography.

The Ir-complex Va-25 (catalyst loading given) and 0.64 g 1-(2,2,4-trimethyl-1-quinolyl)ethanone (3 mmol, purified with heptane: water wash+crystallization) were placed in an 8-mL autoclave vial containing a PTFE-coated stirring bar. The autoclave vial was closed using a screw cap with septum and flushed with argon (10 min). Hexafluoroisopropanol (HFIP, 4 mL) and additive (loading given) were added via the septum to the vial. The vial was placed in an argon containing autoclave and the autoclave was flushed with argon (10 min). The autoclave was pressurized with hydrogen gas (10 bar) and subsequently depressurized to atmospheric pressure three times. After this the autoclave was pressurized to 60 bar hydrogen pressure and was placed in a suitable alumina block. After heating to 85° C. the reaction was kept at this temperature for the given time. After cooling to room temperature and depressurizing, the vial was taken out of the autoclave and the reactions outcome was determined by GC-FID analysis (deluted with EtOH) and the enantiomeric excess by HPLC analysis. Typical values are given.

TABLE 2

| Example | Additive (mol %) | Reaction time (h) | catalyst loading (mol %) | Conversion GC (% a/a) | Enantiomeric excess (% ee) |
|---|---|---|---|---|---|
| 1 | — | 16 | 0.02 | 95.3 | n.d. |
| 2 | — | 21 | 0.02 | 95.5 | n.d. |
| 3 | — | 3 | 0.02 | 55.2 | n.d. |
| 4 | — | 16 | 0.03 | 97.6 | n.d. |
| 5 | Pentafluorophenol (1) | 16 | 0.02 | 97.2 | n.d. |
| 6 | 1,2,2,6,6-Pentamethylpiperidin (1) | 16 | 0.02 | 67.1 | n.d. |
| 7 | Nonafluoro-tert-butyl alcohol (1) | 16 | 0.03 | 96.3 | n.d. |
| 8 | Nonafluoro-tert-butyl alcohol (5) | 16 | 0.03 | 97.5 | n.d. |
| 9 | 3,5-bis-trifluorophenol (1) | 16 | 0.02 | 95.7 | n.d. |
| 10 | AcOH (1) | 16 | 0.02 | 96 | n.d. |
| 11 | AcOH (5) | 3 | 0.02 | 66.5 | n.d. |
| 12 | AcOH (10) | 3 | 0.02 | 63.7 | n.d. |
| 13 | AcOH (20) | 3 | 0.02 | 54.2 | n.d. |
| 14 | $HPF_6$ (1) | 3 | 0.02 | >99 | n.d. |
| 15 | $HBF_4$*$OEt_2$ (1) | 16 | 0.02 | 90.5 | n.d. |
| 16 | TfOH (1) | 16 | 0.02 | 76.9 | n.d. |
| 17 | $Sc(OTf)_3$ (1) | 3 | 0.02 | >99 | 99 |
| 18 | $BF_3$*$OEt_2$ (1) | 3 | 0.02 | 98.9 | 98 |
| 19 | $BH_3$*THF (1) | 3 | 0.02 | 69.8 | n.d. |
| 20 | $BF_3$*AcOH (1) | 3 | 0.02 | >99 | n.d. |
| 21 | $BF_3$*n-PrOH (1) | 3 | 0.02 | >99 | n.d. |
| 22 | $Al(OTf)_3$ (1) | 3 | 0.02 | >99 | n.d. |
| 23 | $AlF_3$ (1) | 3 | 0.02 | 65.9 | n.d. |
| 24 | $AlMe_3$ (1) | 3 | 0.02 | 91.1 | n.d. |
| 25 | $Ti(O^iPr)_4$ (1) | 3 | 0.02 | 90.7 | n.d. |
| 26 | $BPh_3$ (1) | 3 | 0.02 | 85.4 | n.d. |
| 27 | $B(C_6F_5)_3$ (1) | 3 | 0.02 | >99 | 97.6 |
| 28 | $B(C_6F_5)_3$ (0.5) | 3 | 0.02 | 97.3 | n.d. |
| 29 | $B(C_6F_5)_3$ (0.1) | 3 | 0.02 | 63.3 | n.d. |
| 30 | $B(OH)_3$ (1) | 3 | 0.02 | 72.7 | n.d. |

Examples 31-36

The Ir-complex Va-25 (catalyst loading given) and 1-(2,2,4-trimethyl-1-quinolyl)ethanone (amount given; purified with heptane: water wash+crystallization) were placed in an 25-mL autoclave. The autoclave was flushed with argon (10 min). Hexafluoroisopropanol (1.33 mL per mmol of 1-(2,2,4-trimethyl-1-quinolyl)ethenone)) and additive (loading given) were added to the autoclave. The autoclave was pressurized with hydrogen gas (10 bar) and subsequently depressurized to atmospheric pressure three times. After this the autoclave was pressurized to 60 bar hydrogen pressure and was placed in a suitable alumina block. After heating to 85° C. the reaction was kept at this temperature for the given time. After cooling to room temperature and depressurizing, the reactions outcome was determined by GC-FID analysis (deluted with EtOH) and the enantiomeric excess by HPLC analysis.

TABLE 3

| Example | Additive (mol %) | Scale (amount of compound (II)) | Reaction time (h) | catalyst loading (mol %) | Conversion GC (% ala) | Enantiomeric excess (% ee) |
|---|---|---|---|---|---|---|
| 31 | — | 9 mmol | 6 | 0.01 | 50.8 | n.d. |
| 32 | $B(C_6F_5)_3$ (0.5) | 9 mmol | 20 | 0.01 | 85.2 | n.d. |
| 33 | $BF_3$*$OEt_2$ (1) | 10 mmol | 16 | 0.01 | 99.2 | n.d. |
| 34 | $Al(OTf)_3$ (1) | 10 mmol | 16 | 0.01 | >99 | n.d. |
| 35 | $HPF_6$ (1) | 9 mmol | 16 | 0.01 | 97.3 | n.d. |
| 36 | $BF_3$*AcOH (1) | 9 mmol | 16 | 0.01 | 98.1 | n.d. |

Examples 37-54

The Ir-complex (identifier and catalyst loading given) and 0.64 g 1-(2,2,4-trimethyl-1-quinolyl)ethanone (3 mmol, purified with heptane: water wash+crystallization) were placed in an 8-mL autoclave vial containing a PTFE-coated stirring bar. The autoclave vial was closed using a screw cap with septum and flushed with argon (10 min). Hexafluoroisopropanol (HFIP, 4 mL) and $BF_3$*$OEt_2$ (1 mol % with respect to 1-(2,2,4-trimethyl-1-quinolyl)ethanone) were added via the septum to the vial. The vial was placed in an argon containing autoclave and the autoclave was flushed with argon (10 min). The autoclave was pressurized with hydrogen gas (10 bar) and subsequently depressurized to atmospheric pressure three times. After this the autoclave was pressurized to 60 bar hydrogen pressure and was placed in a suitable alumina block. After heating to 85° C. the reaction was kept at this temperature for the given time. After cooling to room temperature and depressurizing, the vial was taken out of the autoclave and the reactions outcome was determined by GC-FID analysis (deluted with EtOH) and the enantiomeric excess by HPLC analysis. Typical values are given.

TABLE 4

| Example | Catalyst | Additive (mol %) | Reaction time (h) | catalyst loading (mol %) | Conversion GC ( % a/a) | Enantiomeric excess (% ee) |
|---|---|---|---|---|---|---|
| 37 | Va-26 | — | 3 | 0.02 | 78.8 | 98.8 |
| 38 | Va-26 | $BF_3$*$OEt_2$ (1) | 3 | 0.02 | 94.2 | 99 |
| 39 | Va-22 | — | 3 | 0.02 | 85.2 | 98.5 |
| 40 | Va-22 | $BF_3$*$OEt_2$ (1) | 3 | 0.02 | >99 | 98.7 |
| 41 | Va-15 | — | 16 | 0.025 | 9.4 | n.d. |
| 42 | Va-15 | — | 16 | 0.05 | 34.6 | 83.2 |
| 43 | Va-15 | $BF_3$*$OEt_2$ (1) | 16 | 0.025 | 82 | 89.2 |
| 44 | Vb-7 | — | 16.5 | 0.025 | 79.5 | 97.5 |
| 45 | Vb-7 | $BF_3$*$OEt_2$ (1) | 16 | 0.025 | >99 | 98.3 |
| 46 | Va-9 | — | 16.5 | 0.025 | 81.7 | 97.9 |
| 47 | Va-9 | $BF_3$*$OEt_2$ (1) | 16 | 0.025 | >99 | 98.8 |
| 48 | Va-11 | — | 16.5 | 0.025 | 42.2 | 94.5 |
| 49 | Va-11 | $BF_3$*$OEt_2$ (1) | 16 | 0.025 | 82.4 | 97.7 |
| 50 | Va-21 | — | 16 | 0.025 | 74 | 98 |
| 51 | Va-21 | $BF_3$*$OEt_2$ (1) | 16 | 0.025 | >99 | 99.4 |
| 52 | Vb-5 | — | 16 | 0.025 | 64.4 | n.d. |
| 53 | Vb-5 | — | 16 | 0.05 | 98.4 | 96.8 |
| 54 | Vb-5 | $BF_3$*$OEt_2$ (1) | 16 | 0.025 | >99 | 97.7 |

Examples 55-58

The Ir-complex Va-25 (0.02 mol %, 0.6 mol) and 0.64 g 1-(2,2,4-trimethyl-1-quinolyl)ethanone (3 mmol, purified with heptane: water wash+crystallization) were placed in an 8-mL autoclave vial containing a PTFE-coated stirring bar. The autoclave vial was closed using a screw cap with septum and flushed with argon (10 min). 2,2,2-Trifluoroethanol (TFE, 4 mL) and $BF_3$*$OEt_2$ (loading given) were added via the septum to the vial. The vial was placed in an argon containing autoclave and the autoclave was flushed with argon (10 min). The autoclave was pressurized with hydrogen gas (10 bar) and subsequently depressurized to atmospheric pressure three times. After this the autoclave was pressurized to 60 bar hydrogen pressure and was placed in a suitable alumina block. After heating to 85° C. the reaction was kept at this temperature for 3 h. After cooling to room temperature and depressurizing, the vial was taken out of the autoclave and the reactions outcome was determined by GC-FID analysis (deluted with EtOH) and the enantiomeric excess by HPLC analysis. Typical values are given.

TABLE 5

| Example | $BF_3$*$OEt_2$ (mol %) | Conversion GC (% a/a) |
|---|---|---|
| 55 | — | <1 |
| 56 | 1 | 86 |
| 57 | 3 | 88 |
| 58 | 5 | 82 |

Examples 59 and 60

Iridium catalyst (1) from DE112015001290 T5 is an example of the catalyst structures of formula (IXb). Also using this catalyst the presence of $BF_3$*$OEt_2$ has a strong influence on conversion and a slightly positive influence on ee (General conditions: 0.2 mol % catalyst (I) from DE112015001290 T5, 40° C., 30 bar $H_2$, starting material concentration 0.1 M in trifluoroethanol)

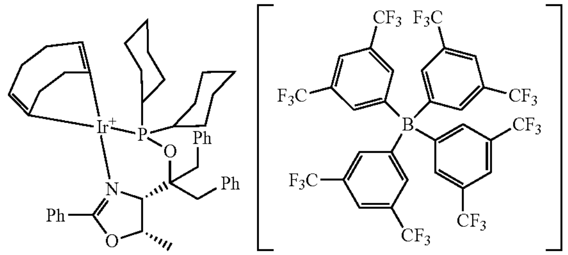

Ir catalyst (1) from DE112015001290 T5

TABLE 5

| Example | Additive | Reaction time | Conv. [%] | ee [%] |
|---|---|---|---|---|
| Example 59-1 | — | 4 h | 33 | 79 |
| Example 59-2 | — | 16 h | 35 | 79 |
| Example 60-1 | 1 mol % $BF_3$*$OEt_2$ | 4 h | 75 | 83 |
| Example 60-2 | 1 mol % $BF_3$*$OEt_2$ | 16 h | 80 | 82 |

The invention claimed is:

1. A process for preparing a compound of formula (Ia) or (Ib), (Ia)

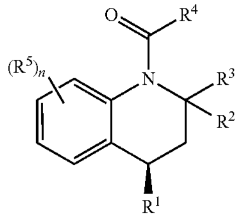

(Ib)

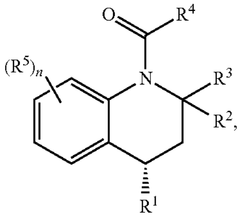

wherein $R^1$ is $C_1$-$C_6$-alkyl, $R^2$ and $R^3$ are the same and are selected from $C_1$-$C_4$ alkyl, $R^4$ is $C_1$-$C_4$-alkyl, $C_1$-$C_4$-haloalkyl, $C_1$-$C_4$-alkoxy, $C_1$-$C_4$-haloalkoxy, phenyl or benzyl, n is 0, 1, or 2, each substituent $R^5$, if present, is independently selected from the group consisting of halogen, $C_1$-$C_6$-alkyl, and $C_1$-$C_6$-haloalkyl, comprising enantioselective hydrogenation of a compound of formula (II)

(II)

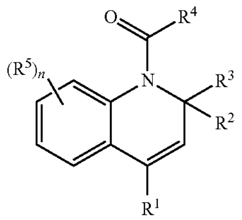

wherein the substituents $R^1$, $R^2$, $R^3$, $R^4$, $R^5$ and the integer n are each as defined for the compound of formula (Ia) or (Ib), in presence of a chiral iridium catalyst, wherein the chiral iridium catalyst comprises a chiral ligand of formula (IIIa), (IIIb), (IXa) or (IXb), (IIIa)

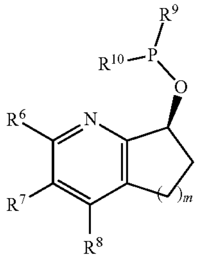

(IIIb)

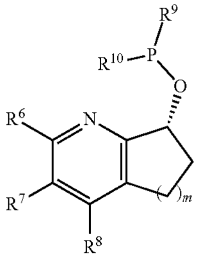

(IXa)

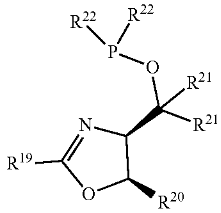

(IXb)

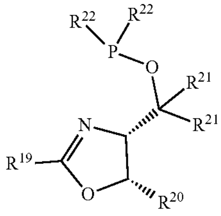

wherein $R^6$ is selected from the group consisting of 1-naphtyl, 2-naphtyl, 9-antracenyl, 9-phenantryl or phenyl, which is unsubstituted or substituted by one to five substituents selected from the group consisting of halogen, $C_1$-$C_4$-alkoxy, $C_1$-$C_4$-alkyl, $C_1$-$C_4$-haloalkyl and phenyl, wherein the phenyl is unsubstituted or substituted by one to five $C_1$-$C_6$-alkyl substituents, $R^7$ and $R^8$ are independently from one another hydrogen or $C_1$-$C_6$-alkyl, $R^9$ and $R^{10}$ are independently from one another selected from the group consisting of ethyl, iso-propyl, sec-butyl, iso-butyl, tert-butyl, cyclohexyl, cyclopentyl, adamantyl and benzyl, and m is 1 or 2, $R^{19}$ is phenyl or t-butyl, $R^{20}$ is hydrogen or methyl, each $R^{21}$ is independently selected from benzyl and methyl, each $R^{22}$ is cyclohexyl, and in the presence of an additive, wherein the additive is selected from the group consisting of hexafluorophosphoric acid, pentafluorophenol, 3,5-bis(trifluoromethyl)phenol, triphenylborane, tris(2,3,4,5,6-pentafluoro-phenyl)borane, aluminum (III) trifluoromethanesulfonate, scandium (III) trifluoromethanesulfonate, aluminum (III) fluoride, titanium (IV) isopropoxide, trimethyl aluminum, boron trifluoride, boron trifluoride diethylether, boron trifluoride acetic acid and boron trifluoride n-propanol, and mixtures thereof.

2. The process according to claim 1, wherein $R^1$ is $C_1$-$C_4$-alkyl, $R^2$ and $R^3$ are methyl, $R^4$ is $C_1$-$C_4$-alkyl, n is 0 or 1, $R^5$ if present, is fluorine, and wherein the chiral iridium catalyst comprises a chiral ligand of formula (IIIa), (IIIb), (IXa), or (IXb), (IIIa)

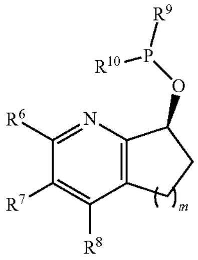

(IIIb)

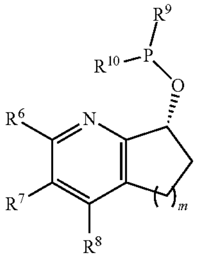

(IXa)

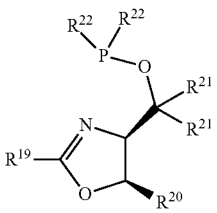

-continued (IXb)

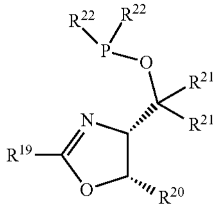

wherein $R^6$ is selected from the group consisting of phenyl, 2,6- or 3,5-dimethylphenyl, 2,4,6-trimethylphenyl, 4-tert-butylphenyl, 4-methoxyphenyl, 3,5-bis-tert-butyl-4-methoxyphenyl, 4-tert-butyl-2,6-dimethylphenyl, 4-fluorophenyl, 4-trifluoromethylphenyl, 1-naphtyl, 9-antracenyl 2,4,6-triisopropylphenyl, 9-phenantryl and 2,6-diethyl-4-methylphenyl, $R^7$ is hydrogen, $R^8$ is hydrogen or methyl, $R^9$ and $R^{10}$ are each the same and selected from the group consisting of ethyl, iso-propyl, tert-butyl, cyclopentyl, adamantyl and cyclohexyl, m is 1, $R^{19}$ is phenyl, $R^{20}$ is methyl, $R^{21}$ is benzyl, $R^{22}$ is cyclohexyl, and wherein the additive is selected from the group consisting of aluminum (III) trifluoromethanesulfonate, scandium (III) trifluoromethanesulfonate, tris(2,3,4,5,6-pentafluorophenyl)borane, hexafluorophosphoric acid, boron trifluoride, boron trifluoride-diethylether, boron trifluoride acetic acid and boron trifluoride n-propanol.

3. The process according to claim 1, wherein $R^1$ is methyl, ethyl or n-propyl, $R^2$ and $R^3$ are methyl, $R^4$ is $C_1$-$C_4$-alkyl, n is 0, 1 or 2, each substituent $R^5$, if present, is independently selected from the group consisting of halogen and $C_1$-$C_6$-alkyl.

4. The process according to claim 1, wherein the hydrogenation is conducted using hydrogen gas at a pressure of from 1 to 300 bar.

5. The process according to claim 1, wherein the amount of chiral iridium catalyst used is within a range of from 0.001 mol % to 5 mol %, based on the amount of the compound of formula (II).

6. The process according to claim 1, wherein the hydrogenation is conducted at a temperature within a range of from 20° C. to 130° C.

7. The process according to claim 1, wherein the hydrogenation is conducted in presence of a solvent selected from the group consisting of 2,2,2-trifluoroethanol, 1,1,1,3,3,3-hexafluoro-2-propanol, 1,2-dichloroethane, tetrafluoropropanol, and mixtures thereof.

8. The process according claim 1, wherein the chiral iridium catalyst has formula (Va) or (Vb):

(Va)

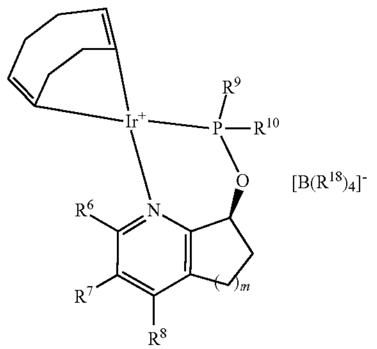

(Vb)

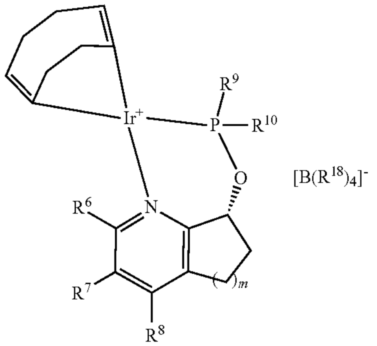

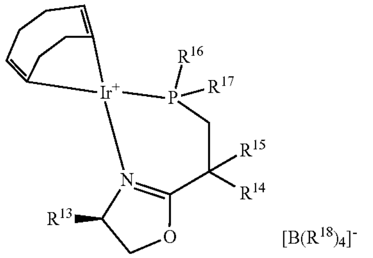

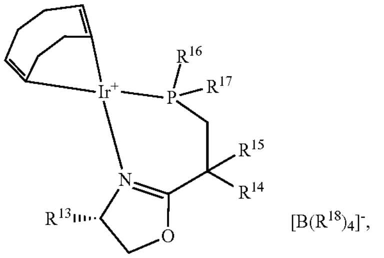

wherein $R^6$ is selected from the group consisting of 1-naphtyl, 2-naphtyl, 9-antracenyl, 9-phenantryl and phenyl, wherein 1-naphtyl, 2-naphtyl, 9-antracenyl, 9-phenantryl and phenyl are unsubstituted or substituted by one to five substituents selected from the group consisting of halogen, $C_1$-$C_4$-alkoxy, $C_1$-$C_4$-alkyl, $C_1$-$C_4$-haloalkyl and phenyl, wherein the phenyl is unsubstituted or substituted by one to five $C_1$-$C_6$-alkyl substituents, $R^7$ and $R^8$ are independently from one another hydrogen or $C_1$-$C_6$-alkyl, $R^9$ and $R^{10}$ are independently from one another selected from the group consisting of ethyl, iso-propyl, sec-butyl, iso-butyl, tert-butyl, cyclohexyl, cyclopentyl, adamantyl and benzyl, m is 1 or 2, $R^{18}$ is phenyl, which is unsubstituted or substituted with one to five substituents selected from fluorine and $C_1$-$C_4$-haloalkyl.

9. The process according to claim 8, wherein $R^6$ is selected from the group consisting of phenyl, 2,6- or 3,5-dimethylphenyl, 2,4,6-trimethylphenyl, 4-tert-butylphenyl, 4-methoxyphenyl, 3,5-bis-tert-butyl-4-methoxyphenyl, 4-tert-butyl-2,6-dimethylphenyl, 4-fluorophenyl, 4-trifluoromethylphenyl, 1-naphtyl, 9-antracenyl 2,4,6-triisopropylphenyl, 9-phenantryl and 2,6-diethyl-4-methylphenyl, $R^7$ is hydrogen, $R^8$ is hydrogen or methyl, $R^9$ and $R^{10}$ are each the same and selected from the group consisting of tert-butyl, adamantyl, cyclopentyl or and cyclohexyl, m is 1 or 2, and $R^{18}$ is 3,5-bis(trifluoromethyl)phenyl.

10. The process according to claim 1, wherein the chiral iridium catalyst comprises a chiral ligand of the formula (IIIa) or (IIIb), wherein $R^6$ is selected from the group consisting of 1-naphtyl, 2-naphtyl, 9-antracenyl, 9-phenantryl and phenyl, which is unsubstituted or substituted by one to five substituents selected from the group consisting of halogen, $C_1$-$C_4$-alkoxy, $C_1$-$C_4$-alkyl, $C_1$-$C_4$-haloalkyl and phenyl, wherein the phenyl is unsubstituted or substituted by one to five $C_1$-$C_6$-alkyl substituents, $R^7$ and $R^8$ are independently from one another hydrogen or $C_1$-$C_6$-alkyl, $R^9$ and $R^{10}$ are independently from one another selected from the group consisting of ethyl, iso-propyl, sec-butyl, iso-butyl, tert-butyl, cyclohexyl, cyclopentyl, adamantyl and benzyl, and m is 1 or 2.

11. The process according to claim 10, wherein $R^6$ is selected from the group consisting of phenyl, 2,6- or 3,5-dimethylphenyl, 2,4,6-trimethylphenyl, 4-tert-butylphenyl, 4-methoxyphenyl, 3,5-bis-tert-butyl-4-methoxyphenyl, 4-tert-butyl-2,6-dimethylphenyl, 4-fluorophenyl, 4-trifluoromethylphenyl, 1-naphtyl, 9-antracenyl 2,4,6-triisopropylphenyl, 9-phenantryl and 2,6-diethyl-4-methylphenyl, $R^7$ is hydrogen, $R^8$ is hydrogen or methyl, $R^9$ and $R^{10}$ are each the same and selected from the group consisting of tert-butyl, cyclopentyl or and cyclohexyl, and m is 1.

12. The process according claim 1, wherein the amount of additive used is within a range of from 0.1 to 10 mol %, based on the amount of the compound of formula (II).

* * * * *